US012799073B2

(12) United States Patent
Matulis et al.

(10) Patent No.: US 12,799,073 B2
(45) Date of Patent: Nov. 17, 2026

(54) TARGETED COVALENT INHIBITORS FOR CARBONIC ANHYDRASES

(71) Applicant: VILNIUS UNIVERSITY, Vilnius (LT)

(72) Inventors: Daumantas Matulis, Vilnius (LT); Virginija Dudutienė, Vilnius (LT); Aivaras Vaškevičius, Jonava (LT); Asta Zubrienė, Vilnius (LT); Denis Baronas, Vilnius (LT)

(73) Assignee: Vilnius University, Vilnius (LT)

( * ) Notice: Subject to any disclaimer, the term of this patent is extended or adjusted under 35 U.S.C. 154(b) by 587 days.

(21) Appl. No.: 18/455,109

(22) Filed: Aug. 24, 2023

(65) Prior Publication Data

US 2025/0066291 A1 Feb. 27, 2025

(51) Int. Cl.
*C07C 317/32* (2006.01)
*C07C 317/14* (2006.01)
*C07C 317/18* (2006.01)
*C07C 317/22* (2006.01)
*C07C 317/36* (2006.01)

(52) U.S. Cl.
CPC .......... *C07C 317/32* (2013.01); *C07C 317/14* (2013.01); *C07C 317/18* (2013.01); *C07C 317/22* (2013.01); *C07C 317/36* (2013.01)

(58) Field of Classification Search
None
See application file for complete search history.

(56) References Cited

U.S. PATENT DOCUMENTS 9,725,467 B2 8/2017 Matulis et al.
2015/0266900 A1* 9/2015 Matulis ................. C07C 311/39 564/81

FOREIGN PATENT DOCUMENTS

EP 2914583 B1 2/2019

OTHER PUBLICATIONS

Janoniene, A. et al., "A versatile carbonic anhydrase IX targeting ligand-functionalized porous silicon nanoplatform for dual hypoxia cancer therapy and imaging," Applied Materials & Interfaces, vol. 9, pp. 13976-13987 (2017).*

Dudutiene, V. et al. 2013. 4-substituted-2,3,5,6-tetrafluorbenzenesulfonamides as inhibitors of cabonic anydrases I, II, VI, XII, and XIII. Biorganic & Medicinal Chemistry 21: 2093-2106.

Dudutiene, V. et al. 2015. Functionalization of fluorinated benzenesulfonamides and their inhibitory properties towrd carbonic anhydrases. ChemMedChem 10: 662-687.

Zubriene, A. et al. 2016. Intrinsic thermodynamics and structures of 2,4,- and 3,4-substituted fluorinated benzenesulfonamides binding to carbonic anhydrases. ChemMedChem 11: 1-7.

Dudutiene, V. et al. 2014.Discovery and characteization of novel selective inhibitors of carbonic anydrase IX. J.Med. Chem. 57:9435-9446.

Gedgaudas M. et al. 2022. Thermott: A comprehensive online tool for potein-ligand binding constant determination. Drug Discovery Today. vol. 27, No. 8: 2076-2079.

* cited by examiner

*Primary Examiner* — John Pak
(74) *Attorney, Agent, or Firm* — Koivula & Somersalo LLC

(57) ABSTRACT

This invention teaches a class of fluorinated benzenesulfonamides of general structure I, as shown:

I

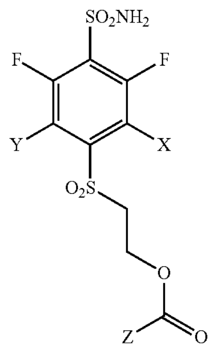

which are useful for binding and inhibiting carbonic anhydrases irreversibly. The compounds taught can be used in pharmaceutical compositions in effective amounts to treat diseases/disorders responsive to the inhibition of human carbonic anhydrases.

5 Claims, 2 Drawing Sheets

TARGETED COVALENT INHIBITORS FOR CARBONIC ANHYDRASES

FIELD OF THE INVENTION

Field of the invention relates to compounds that are precursors (designed/designated as prodrugs) of active compounds (designed/designated as pharmaceuticals), in particular, compounds being used as active ingredients of pharmaceutical preparation to irreversibly bind and inhibit isozymes of carbonic anhydrase for treatment of conditions responsive to the inhibition of carbonic anhydrases.

BACKGROUND OF THE INVENTION

Carbonic anhydrases (CAs) are present in all living organisms, acting as catalysts for the reversible hydration of $CO_2$. There are fifteen carbonic anhydrase isozymes identified in humans—twelve catalytically active and three inactive carbonic anhydrases. Carbonic anhydrases are involved in a broad range of physiological and pathological functions, therefore some isozymes (e.g., CA II, IV, VA, VB, VII, IX, XII, XIII and XIV) constitute targets for the development of drugs. Carbonic anhydrase inhibitors (CAIs) are used as diuretics, systemic and topically acting antiglaucoma agents, and are considered as valid therapeutic agents against obesity, kidney dysfunction, migraine, neurological disorders and epilepsy. Furthermore, some compounds are in clinical development for the treatment of hypoxic, metastatic cancers. Recently, progress was achieved according to the treatment of conditions for which few or no therapeutic opportunities are available, such as neuropathic pain, cerebral ischemia, and some forms of arthritis.

The major class of CAIs is aromatic and heterocyclic sulfonamides involved in reversible interaction with the enzyme. The strong interaction of such compounds is based on the capability of the primary sulfonamide group to coordinate with zinc in the binding site. Due to this feature, the irreversible mode of inhibition of CAs was not considered as a priority or inevitable need. However, irreversible covalent binding can be superior due to the prolonged action of active compound, enhanced potency, possibility to achieve full target occupancy, and decreased competitivity in the environment with a high concentration of natural substrate.

The development of covalent CA inhibitors began half a century ago using the brominated compounds, bromoacetate, bromoacetazolamide and N-bromoacetylacetazolamide, which may participate in alkylation reactions. Unfortunately, the discovery of covalent inhibitors almost stopped where it began and covalent inhibitors are poorly investigated among all CA isozymes. However, some advances have been made in protein labeling using CA as a model protein and attaching probes via the covalent mode. These investigations are not directly related to the field expansion of CA inhibitors but can contribute to the development of covalent inhibitors.

For many years it appeared that covalent inhibitors could cause too many side effects and are unlikely to succeed as pharmaceutical agents. However, rational design of covalent inhibitors, known as the design of targeted covalent inhibitors (TCIs), opened a new era for covalent drug development. TCIs are generated from optimized reversible ligands modified by attachment of an electrophilic reactive group; warhead. Such warhead is expected to address proximal amino acid, most frequently cysteine, lysine, tyrosine, serine, threonine, or histidine. Thus, high affinity and selectivity compounds explored as reversible inhibitors can be repurposed into targeted covalent inhibitors.

In related publications (Dudutienė, V. et al. *Bioorg. Med. Chem.* 21, 2093-2106 (2013); EP2914583 (B1)), fluorinated benzenesulfonamides were discovered as highly potent CA inhibitors. In another related publication (Dudutienė, V. et al. *ChemMedChem,* 10, 662-687 (2015); Dudutienė, V. et al. *J. Med. Chem.,* 57, 9435-9446 (2014); EP2914583 (B1)), it was shown that attachment of various substituents on fluorinated benzenesulfonamide scaffold led to isozyme-selective inhibitors. The cited publications teach high affinity and selectivity compounds but do not teach how to use TCIs to treat diseases by inhibiting CAs enzymatic activity.

SUMMARY OF THE INVENTION

The present description teaches compounds for the prevention and/or treatment of diseases/disorders related to inhibition of carbonic anhydrase. In the present disclosure, fluorinated benzenesulfonamides were found useful for inhibiting carbonic anhydrases. These compounds are highly effective as inhibitors due to their irreversible mode of action. The pharmacological action of these compounds makes them useful for treating conditions responsive to the inhibition of carbonic anhydrases; e.g., glaucoma, macular edema, cataract, retinopathy, infantile nystagmus syndrome (INS), retinal/cerebral edema, edema, acute mountain sickness, bipolar disorder, chronic obstructive pulmonary disease (COPD), gastric ulcer, obesity, epilepsy, sleep apnea, migraine, hemorrhagic stroke, diabetic injury, congestive heart failure, pulmonary hypertension, cariogenesis, ischemic and hemorrhagic brain injury, osteoporosis, cancers and etc.

DETAILED DESCRIPTION OF THE INVENTION

Figure 1:
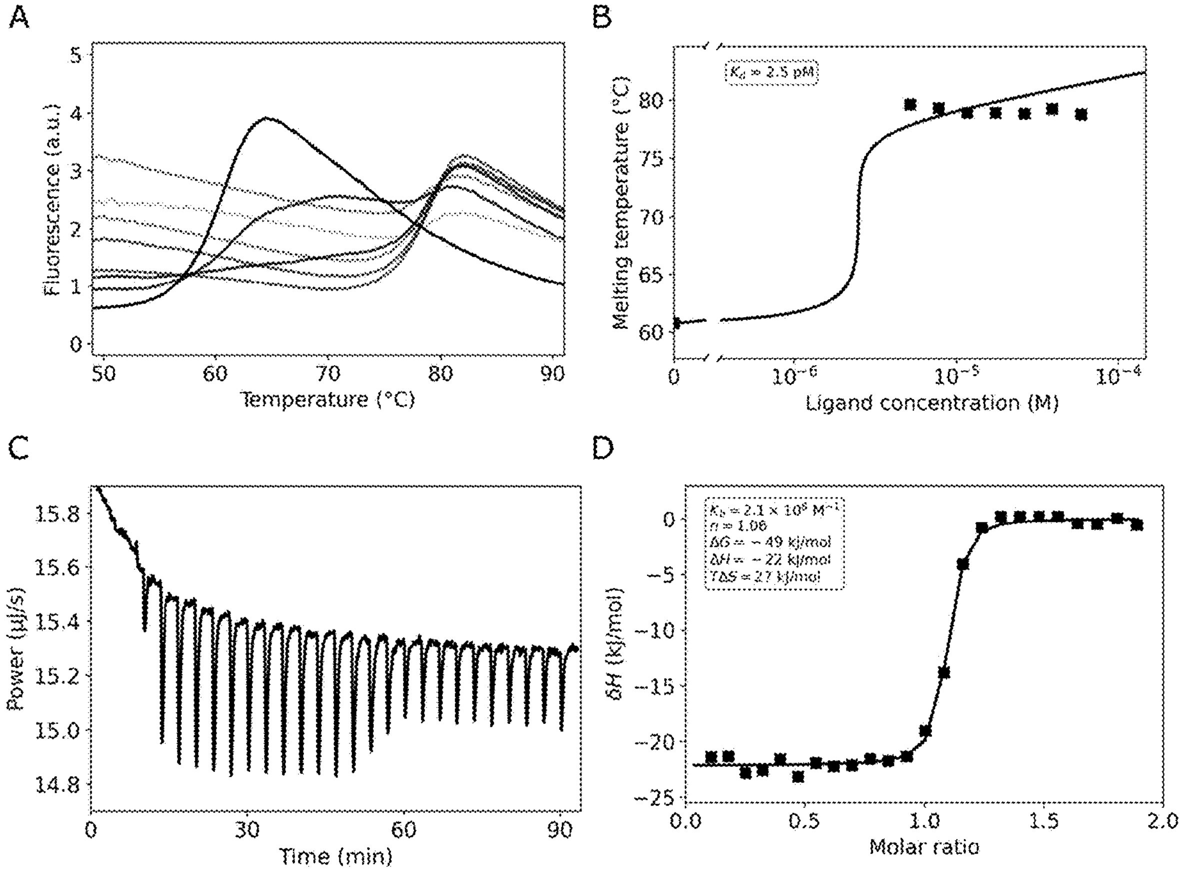
FIG. 1A-D shows binding to CAIX isozyme by FTSA and ITC. A, B—FTSA data of AV21-47 binding to CAIX. A—Raw data of CAIX unfolding in the presence of different compound concentrations. B—dependence of CAIX melting temperature $T_m$ on ligand concentration. C, D—Binding of AV19-37 to CAIX as determined by isothermal titration calorimetry. C—raw ITC curve at pH 7.0, TRIS chloride buffer, at 37 °C. D—Integrated ITC curve.

Pharmaceutical compositions comprising fluorinated benzenesulfonamides are designed herein to covalently bind and inhibit carbonic anhydrases. The pharmaceutical compositions can be non-toxic, pharmaceutically acceptable salts of the fluorinated benzenesulfonamides, which retain activity comparable to original compounds and do not attain any harmful and undesirable effects.

In the following description of the pharmaceutical compositions, the use of such compositions may be for the treatment of diseases and illnesses that respond to the inhibition of carbonic anhydrases.

The pharmaceutical compositions comprising fluorinated benzenesulfonamide compounds are designed to treat illnesses related to function of human carbonic anhydrases. The fluorinated benzenesulfonamide compounds have the general structure shown in formula I:

I

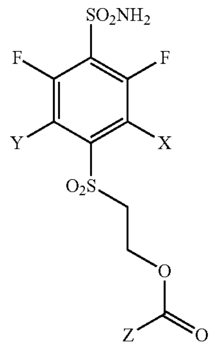

Wherein Y, X are F or $NHR^1$, $NR^1R^2$ and Z is $R^3$ or $NHR^3$;

$R^1$, $R^2$ is $R^4$, $R^5$, $R^6$, $R^7$ $R^4$ is cycloalkyl, cycloalkenyl, cycloalkynyl, heterocycloalkyl, heterocycloalkenyl or heterocycloalkynyl, each of which is unfused or fused with benzene, each of ring is unsubstituted or substituted on one or more carbon atoms with substituent independently chosen from $R^{12}$;

$R^5$ is alkyl, alkenyl or alkynyl each of which is unsubstituted or substituted on one or more carbon atoms with substituent independently chosen from $R^{12}$;

$R^6$ is phenyl, which is unfused or fused with benzene, heteroarene, cycloalkane or heterocycloalkane each of which is unsubstituted or substituted on one or more ring carbon atoms with substituent independently chosen from $R^{12}$;

$R^7$ is alkylphenyl, alkylheteroaryl each of which is unsubstituted or substituted on one or more carbon atoms with substituent independently chosen from $R^{12}$;

$R^3$ is $R^8$, $R^9$, $R^{10}$, $R^{11}$ $R^8$ is cycloalkyl, cycloalkenyl, cycloalkynyl, heterocycloalkyl, heterocycloalkenyl or heterocycloalkynyl, each of which is unfused or fused with benzene, each of ring is unsubstituted or substituted on one or more carbon atoms with substituent independently chosen from $R^{12}$;

$R^9$ is alkyl, alkenyl or alkynyl each of which is unsubstituted or substituted on one or more carbon atoms with substituent independently chosen from $R^{12}$;

$R^{10}$ is phenyl, which is unfused or fused with benzene, heteroarene, cycloalkane or heterocycloalkane each of which is unsubstituted or substituted on one or more ring carbon atoms with substituent independently chosen from $R^{12}$;

$R^{11}$ is alkylphenyl, alkylheteroaryl each of which is unsubstituted or substituted on one or more carbon atoms with substituent independently chosen from $R^{12}$;

$R^{12}$ is F, Cl, Br, I, OH, $OR^{13}$, SH, $SR^{13}$, $S(O)R^{13}$, $SO_2R^{13}$, $C(O)R^{13}$, $C(O)OR^{13}$, $OC(O)R^{13}$, $C(O)N(R^{13})_2$, $C(O)NHR^{13}$, $C(O)N(CH_3)R^{13}$, $NHC(O)R^{13}$, $NR^{13}C(O)R^{13}$, $NHC(O)OR^{13}$, $NR^{13}C(O)OR^{13}$, $OC(O)N(R^{13})_2$, $OC(O)NHR^{13}$, $OC(O)NH_2$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $SO_2NH_2$, $SO_2NHR^{13}$, $SO_2N(R^{13})_2$, $NR^{13}SO_2R^{13}$, $NHSO_2NHR^{13}$, $NHSO_2N(R^{13})_2$, $NR^{13}SO_2NHR^{13}$, $NR^{13}SO_2N(R^{13})_2$, C(O)NHNHOH, $C(O)NHNHOR^{13}$, $C(O)NHSO_2R^{13}$, $C(O)NR^{13}SO_2R^{13}$, $C(NH)NH_2$, $C(NH)NHR^{13}$, $C(NH)N(R^{13})_2$, $N(CH_3)SO_2NHR^{13}$, $NHSO_2N(CH_3)R^{13}$, $N(CH_3)SO_2N(CH_3)R^{13}$, $NH_2$, $NHR^{13}$, $N(R^{13})_2$, $N(CH_3)C(O)N(R^{13})_2$, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$;

$R^{13}$ is alkyl, alkenyl or alkynyl, cycloalkyl, cycloalkenyl, cycloalkynyl, heterocycloalkyl, heterocycloalkenyl or heterocycloalkynyl, alkylphenyl, alkylheteroaryl, phenyl, which is unfused or fused with benzene, heteroarene, cycloalkane or heterocycloalkane.

Compounds of formula I are precursors (designed as prodrugs) capable of forming compounds with active electrophilic groups, creating active compounds that can covalently bond with carbonic anhydrases via Scheme A. The active compound, as shown in structure II, forms in the presence of a nucleophilic amino acid. Compounds of structure II are highly reactive and are eager to interact with nucleophilic amino acids forming covalent bonds. The highly reactive vinylsulfone group is known as a warhead used for the formation of covalent bond between small molecule and nucleophilic amino acid of protein, such as cysteine, lysine, tyrosine, histidine.

Scheme A

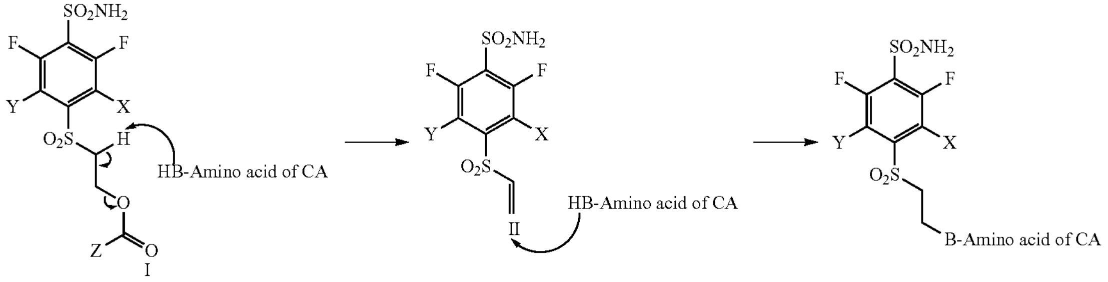

I
II

Scheme A: Transformation of compounds of structure I to compounds of structure II and reaction with the nucleophilic amino acid of carbonic anhydrase (CA) forming a covalent bond between compound II and enzyme. The nucleophilic residue of the enzyme depicted as HB.

Compounds of structure II are highly reactive and unstable and are obtained in situ. A compound of structure II can be one of:

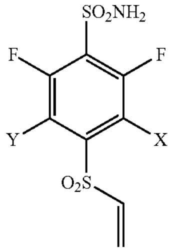

wherein X, Y are F, $NHR^1$; $NR^1R^2$ $R^1$, $R^2$ is $R^4$, $R^5$, $R^6$, $R^7$ $R^4$ is cycloalkyl, cycloalkenyl, cycloalkynyl, heterocycloalkyl, heterocycloalkenyl or heterocycloalkynyl, each of which is unfused or fused with benzene, each of ring is unsubstituted or substituted on one or more carbon atoms with substituent independently chosen from $R^8$.

$R^5$ is alkyl, alkenyl or alkynyl each of which is unsubstituted or substituted on one or more carbon atoms with substituent independently chosen from $R^8$.

$R^6$ is phenyl, which is unfused or fused with benzene, heteroarene, cycloalkane or heterocycloalkane each of which is unsubstituted or substituted on one or more ring carbon atoms with substituent independently chosen from $R^8$.

$R^7$ is alkylphenyl, alkylheteroaryl each of which is unsubstituted or substituted on one or more carbon atoms with substituent independently chosen from $R^8$;

$R^8$ is F, Cl, Br, I, OH, $OR^9$, SH, $SR^9$, $S(O)R^9$, $SO_2R^9$, $C(O)R^9$, $C(O)OR^9$, $OC(O)R^9$, $C(O)N(R^9)_2$, $C(O)NHR^9$, $C(O)N(CH_3)R^9$, $NHC(O)R^9$, $NR^9C(O)R^9$, $NHC(O)OR^9$, $NR^9C(O)OR^9$, $OC(O)N(R^9)_2$, $OC(O)NHR^9$, $OC(O)NH_2$, $NHC(O)NH_2$, $NHC(O)NHR^9$, $NHC(O)N(R^9)_2$, $NR^9C(O)NHR^9$, $NR^9C(O)N(R^9)_2$, $SO_2NH_2$, $SO_2NHR^9$, $SO_2N(R^9)_2$, $NR^9SO_2R^9$, $NHSO_2NHR^9$, $NHSO_2N(R^9)_2$, $NR^9SO_2NHR^9$, $NR^9SO_2N(R^9)_2$, C(O)NHNHOH, $C(O)NHNHOR^9$, $C(O)NHSO_2R^9$, $C(O)NR^9SO_2R^9$, $C(NH)NH_2$, $C(NH)NHR^9$, $C(NH)N(R^9)_2$, $N(CH_3)SO_2NHR^9$, $NHSO_2N(CH_3)R^9$, $N(CH_3)SO_2N(CH_3)R^9$, $NH_2$, $NHR^9$, $N(R^9)_2$, $N(CH_3)C(O)N(R^9)_2$, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$.

$R^9$ is alkyl, alkenyl or alkynyl, cycloalkyl, cycloalkenyl, cycloalkynyl, heterocycloalkyl, heterocycloalkenyl or heterocycloalkynyl, phenyl, which is unfused or fused with benzene, heteroarene, cycloalkane or heterocycloalkane.

Exemplary uses of pharmaceutical compositions comprising compounds taught by structure I include control of conditions where irreversible inhibition of carbonic anhydrases is necessary and characterized in that the conditions are selected from eye disorders such as glaucoma, macular edema, diabetic macular edema, retinitis pigmentosa, hereditary retinoschisis, cataract, retinopathy (including chronic central serous chorioretinopathy, diabetic retinopathy, hypertensive retinopathy) and other disorders including infantile nystagmus syndrome (INS), cerebral edema, edema, acute mountain sickness, bipolar disorder, chronic obstructive pulmonary disease (COPD), gastric ulcer, obesity, epilepsy, sleep apnea, migraine, diabetic injury, congestive heart failure, pulmonary hypertension, cariogenesis, cerebral ischemia, diabetic brain injury, cardiac diseases (including angina, myocardial infarction), idiopathic intracranial hypertension, hydrocephalus, a range of cerebral pathologies, such as traumatic brain injury and ischemic and hemorrhagic stroke, osteoporosis, pseudotumor cerebri, cancers among them renal, pancreatic, esophagus, head and neck, thyroid (including papillary/follicular carcinomas), nasopharygeal, breast, ovarian, vulva, uterine cervix, bladder, skin (including squamous/basal cell carcinomas), liver, lung, brain cancers, and mesothelioma.

General Reaction Schemes

The compounds of structure I can be obtained according to general synthesis schemes B, C.

The compounds bearing an ester group were synthesized according scheme B. Pentafluorobenzenesulfonamide was synthesized from pentafluorobenzensulfonchloride according to literature (Dudutienė, V. et al. *Bioorg. Med. Chem.* 21, 2093-2106 (2013)) via amination reaction using ammonia solution in THF. Selective aromatic nucleophilic substitution in para position was achieved using 2-mercaptoethanol in MeOH with $Et_3N$ followed by sulfide oxidation to sulfone group using $H_2O_2$ solution in acetic acid as described in literature (Dudutienė, V. et al. *Bioorg. Med. Chem.* 21, 2093-2106 (2013)). Compounds 5 were synthesized using a well known fischer esterification method with corresponding alkyl or phenyl carboxylic acid in toluene and few drops of $H_2SO_4$ (conc.). Meta/para substituted sulfonamides bearing ester functional group were synthesized by carrying out aromatic nucleophilic substitution on compound 4 with appropriate cycloalkyl nucleophile in DMSO according to known procedure (Dudutienė, V. et al. *ChemMedChem,* 10, 662-687 (2015); U.S. Pat. No. 9,725,467 (B2); EP2914583 (B1)). Although nucleophilic aromatic substitution reactions were carried out using primary cycloakyl nucleophiles, the use of other nucleophiles are also possible (primary/secondary alkylamines and secondary cycloalkylamines). Furthermore, by increasing reaction temperature it is possible to synthesize di-meta substituted sulfonamides. Afterwards, compounds 7 were synthesized by Fischer esterification reaction with either respective alkyl or phenyl carboxylic acid in toluene and few drops of $H_2SO_4$ (conc.).

Scheme B

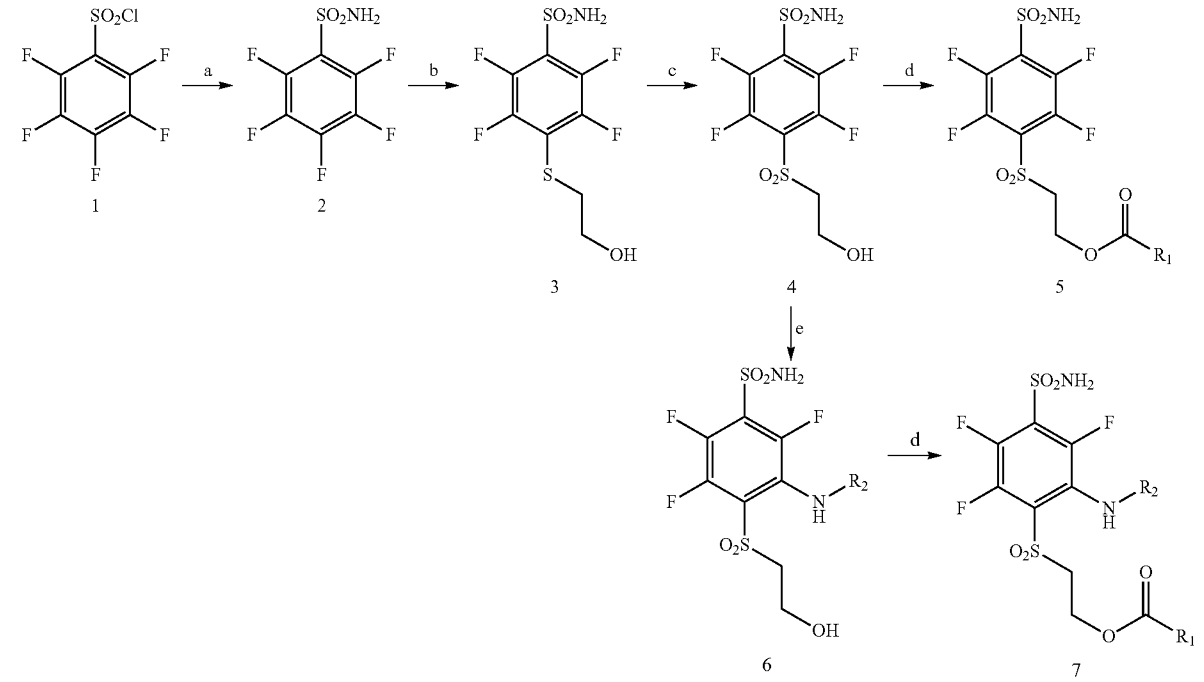

1 2 3 4 5 6 7 a) $NH_3$ aq. (25%), THF; b) $HSCH_2CH_2OH$, MeOH, $Et_3N$; c) $H_2O_2$ (30%), AcOH; d) $R_1COOH$, $H_2SO_4$ (conc.), toluene; e) $NH_2R_2$, DMSO.

The compounds bearing carbamate group were synthesized according scheme C. In order to avoid sulfonylurea byproducts during appropriate carbamate synthesis, the sulfonamide group was protected by forming sulfonimide, compound 8, using methodology mentioned in literature (Dudutienė, V. et al. *Bioorg. Med. Chem.* 21, 2093-2106 (2013)). Para substituted carbamates were synthesized using various phenyl isocyanates, by either refluxing compound 8 in toluene or by carrying out the reaction in MeCN at room temperature with DBTDL as a catalyst. The last step was sulfonamide group deprotection by refluxing compounds 9 in toluene with few drops of HCl (conc.). Although only one example of meta/para substituted sulfonamide bearing carbamate group was synthesized, other meta/para substituted sulfonamides can be synthesized in the same manner. Compound 11 was synthesized identically to compound 6-via aromatic nucleophilic substitution reaction with amine in DMSO at room temperature according to methology (Dudutienė, V. et al. *ChemMedChem,* 10, 662-687 (2015)); U.S. Pat. No. 9,725,467 (B2); EP2914583 (B1)). Afterwards, compound 11 was refluxed with isocianate in toluene to attain compound 12. Sulfonamide group deprotection was achieved by reflux in MeOH with few drops of HCl (conc.).

Scheme C

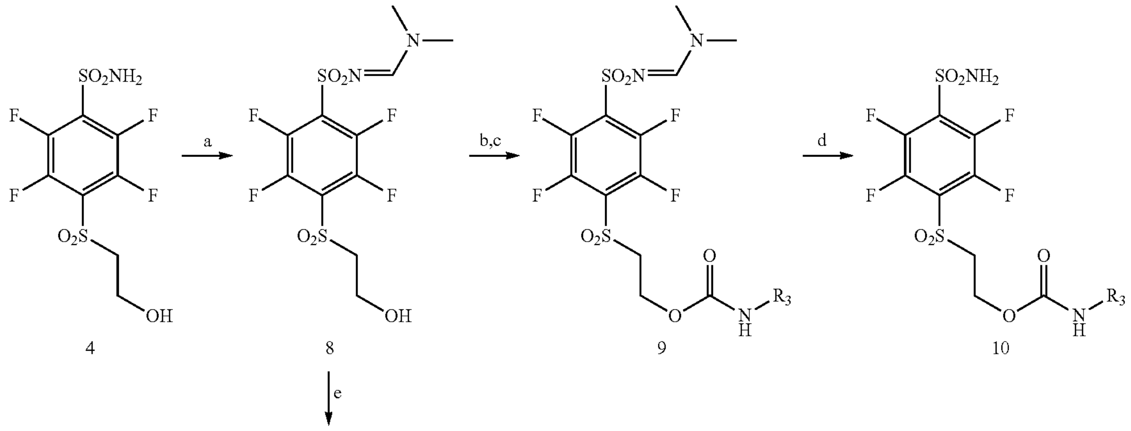

4 8 9 10

-continued

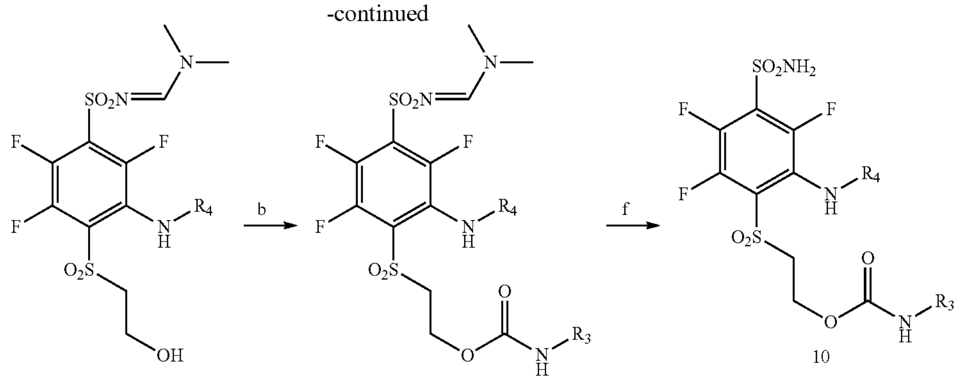

11 12 10 a) $(CH_3O)_2CHN(CH_3)_2$, MeCN; b) $OCNR_3$, toluene; c) $OCNR_3$, DBTDL, MeCN; d) HCl (conc.), Toluene; e) $NH_2R_4$, DMSO; f) HCl (conc.), MeOH.

EXAMPLES

All starting materials and reagents were commercial products or those which could be prepared according to known procedures. Melting points of the compounds were determined in open capillaries on a Thermo Scientific 9100 Series and are uncorrected. $^1H$ and $^{13}C$ NMR spectra were recorded on a Bruker spectrometer (400 and 100 MHz, respectively) in DMSO-$D_6$ or $CDCl_3$ using residual DMSO, $CDCl_3$ signals (2.50 ppm, 7.26 ppm and 39.52 ppm, 77.16 ppm for $^1H$ and $^{13}C$ NMR spectra, respectively) as the internal standard. $^{19}F$ NMR spectra were recorded on a Bruker spectrometer (376 MHz) with $CFCl_3$ as an internal standard. TLC was performed with silica gel 60 F254 aluminum plates (Merck) and visualized with UV light. Column chromatography was performed using silica gel 60 (0.040-0.063 mm, Merck). High-resolution mass spectra (HRMS) were recorded on a Dual-ESI Q-TOF 6520 mass spectrometer (Agilent Technologies). Compound IUPAC names were generated with Chemdraw ultra 12.0.

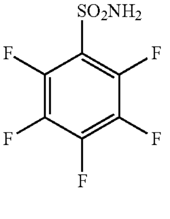 [SMILES: NS(=O)(=O)c1c(F)c(F)c(F)c(F)c1F]

2,3,4,5,6-pentafluorobenzenesulfonamide 2,3,4,5,6-pentafluorobenzenesulfonamide was prepared according to known procedure (Dudutienė, V. et al. *Bioorg. Med. Chem.* 21, 2093-2106 (2013)). The mixture of pentafluorobenzenesulfonyl chloride (1 g, 3.75 mmol) and THF (60 mL) was cooled to ~−10 °C and aqueous ammonia (~1.2 mL, 25%) was added dropwise while stirring. The progress of the reaction was monitored by TLC and the solution pH was kept at pH~7. THF was evaporated in vacuum and the resultant precipitate was washed with cold $H_2O$. Recrystallization was accomplished from $H_2O$. Yield: 0.84 g (90%), mp 156 °C close to the value in the literature (Dudutienė, V. et al. *Bioorg. Med. Chem.* 21, 2093-2106 (2013)), mp 156-157 °C.

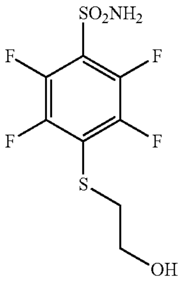 [SMILES: NS(=O)(=O)c1c(F)c(F)c(SCCO)c(F)c1F]

2,3,5,6-tetrafluoro-4-((2-hydroxyethyl)thio)benzenesulfonamide 2,3,5,6-tetrafluoro-4-((2-hydroxyethyl)thio)benzenesulfonamide was prepared according to known procedure in literature (Dudutienė, V. et al. *Bioorg. Med. Chem.* 21, 2093-2106 (2013). 2,3,4,5,6-pentafluorobenzenesulfonamide (1.000 g; 4.05 mmol; 1 eq.), 2-mercaptoethanol (0.341 ml; 4.86 mmol; 1.2 eq.), $Et_3N$ (0.677 ml; 4.86 mmol; 1.2 eq.) were dissolved in MeOH (20 ml) and left stirring at room temperature over night. Next morning additional 2-mercaptoethanol (0.085 ml; 1.21 mmol; 0.3 eq.) and $Et_3N$ (0.169 ml; 1.21 mmol; 0.3 eq.) portions were added and reaction mixture was left stirring for 2 hours. After reaction completion the solvent was evaporated under reduced pressure and resultant precipitate was washed with $H_2O$. Recrystallization was accomplished from $H_2O$. Yield: 1.029 g; (83%). Mp: 111-112 °C (close to the value in the literature (Dudutienė, V. et al. *Bioorg. Med. Chem.* 21, 2093-2106 (2013)), mp: 111-112 °C).

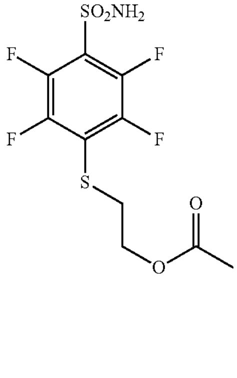 [SMILES: CC(=O)OCCSc1c(F)c(F)c(S(N)(=O)=O)c(F)c1F]

2-((2,3,5,6-tetrafluoro-4-sulfamoylphenyl)thio)ethyl acetate (AV19-36)

2,3,5,6-tetrafluoro-4-((2-hydroxyethyl)thio)benzenesulfonamide (0.104 g; 0.30 mmol; 1 eq.), acetic acid (10 ml) and two drops of $H_2SO_4$ (conc.) were dissolved in toluene (35 ml) and refluxed for 2 hours. The resulting mixture was washed with brine (3×10 ml). The organic phase was dried using anhydrous $Na_2SO_4$ and evaporated under reduced pressure. The product was purified by column chromotography (silica gel, EtOAc/$CHCl_3$ (1:1), Rf=0.76). Yield: 0.078 g; (65%). Mp: 108-110 °C. $^1H$ NMR (400 MHz, DMSO-$d_6$, δ): 1.90 (3H, s, $CH_3$), 3.29 (2H, t, J=5.9 Hz, $SCH_2$), 4.16 (2H, t, J=5.3 Hz, $CH_2O$), 8.44 (2H, s, $SO_2NH_2$). $^{13}C$ NMR (100 MHz, DMSO-$d_6$, δ): 20.27 ($CH_3$), 32.56 ($SCH_2$, t, J($^{19}F$-$^{13}C$)=2.8 Hz), 63.15 ($CH_2O$), 117.89 (C4, t, J($^{19}F$-$^{13}C$)=20.5 Hz), 122.94 (C1, t, J($^{19}F$-$^{13}C$)=15.6 Hz), 142.48 (C3 and C5, ddt, $^1J$($^{19}F$-$^{13}C$)=253.7 Hz, $^2J$($^{19}F$-$^{13}C$)=17.2 Hz, $^3J$($^{19}F$-$^{13}C$)=4.4 Hz), 146.72 (C2 and C6, dd, $^1J$($^{19}F$-$^{13}C$)=240.8 Hz, $^2J$($^{19}F$-$^{13}C$)=13.9 Hz), 169.95 (OC(O)). $^{19}F$ NMR (376 MHz, DMSO-$d_6$, δ): −132.44--132.69 (2F, m), −139.10--139.30 (2F, m). HRMS for $C_{10}H_9F_4NO_4S_2$ [(M−H)$^-$]: calc. 345.9836, found 345.9838.

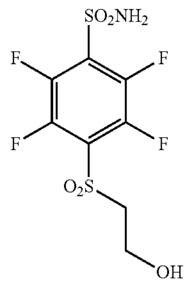 [SMILES: NS(=O)(=O)c1c(F)c(F)c(S(=O)(=O)CCO)c(F)c1F]

2,3,5,6-tetrafluoro-4-((2-hydroxyethyl)sulfonyl)benzenesulfonamide (VD10-35-1)

2,3,5,6-tetrafluoro-4-((2-hydroxyethyl)sulfonyl)benzenesulfonamide was prepared according to known procedure in literature (Dudutienė, V. et al. *Bioorg. Med. Chem.* 21, 2093-2106 (2013)). 2,3,5,6-tetrafluoro-4-((2-hydroxyethyl)thio)benzenesulfonamide (1.542 g; 5.06 mmol; 1 eq.) was dissolved in acetic acid (30 ml) and heated at 75 °C for 18 hours. $H_2O_2$ (30%) was added by portions (0.1 ml) every 30 minutes (overall 3.6 ml) until complete starting material conversion. Afterwards, the solvent was evaporated under reduced pressure and the product was purified by column chromatography (silica gel, EtOAc/$CHCl_3$ (1:1), Rf=0.13). Yield: 0.768 g; (45%). Mp: 138-139 °C (close to the value in the literature (Dudutienė, V. et al. *Bioorg. Med. Chem.* 21, 2093-2106 (2013)), mp: 139-140 °C).

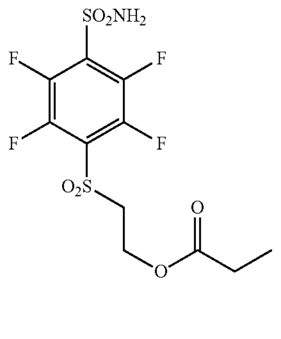 [SMILES: CCC(=O)OCCS(=O)(=O)c1c(F)c(F)c(S(N)(=O)=O)c(F)c1F]

2-((2,3,5,6-tetrafluoro-4-sulfamoylphenyl)sulfonyl)ethyl propionate (AV21-03-2)

2,3,5,6-tetrafluoro-4-((2-hydroxyethyl)sulfonyl)benzenesulfonamide (VD10-35-1) (0.152 g; 0.451 mmol), propionic acid (2 ml) and three drops of $H_2SO_4$ (conc.) were dissolved in toluene (25 ml) and refluxed for 1 hour. The resulting mixture was washed with brine (3×10 ml). The organic phase was dried using anhydrous $Na_2SO_4$ and evaporated under reduced pressure. The product was purified by column chromotography (silica gel, EtOAc/$CHCl_3$ (1:1), Rf=0.74). Yield: 0.0448 g; (25%). Mp: 109-111 °C. $^1H$ NMR (400 MHz, DMSO-$d_6$, δ): 0.93 (3H, t, J=7.5 Hz, $CH_3$), 2.08 (2H, q, J=7.5 Hz, $CH_2CH_3$), 4.03 (2H, t, J=5.6 Hz, $SO_2CH_2$), 4.42 (2H, t, J=5.6 Hz, $CH_2O$), 8.69 (2H, s, $SO_2NH_2$). $^{13}C$ NMR (100 MHz, DMSO-$d_6$, δ): 8.63 ($CH_3$), 26.36 ($CH_2CH_3$), 56.00 ($SO_2CH_2$), 57.22 ($CH_2O$), 121.32 (C1, t, J($^{19}F$-$^{13}C$)=14.6 Hz), 127.85 (C4, t, J($^{19}F$-$^{13}C$)=15.2 Hz), 142.90 (C2 and C6, dd, $^1J$($^{19}F$-$^{13}C$)=256.1 Hz, $^2J$($^{19}F$-$^{13}C$)=18.8 Hz), 144.36 (C2 and C5, dd, $^1J$($^{19}F$-$^{13}C$)=259.1 Hz, $^2J$($^{19}F$-$^{13}C$)=20.4 Hz), 172.82 (OC(O)). $^{19}F$ NMR (376 MHz, DMSO-$d_6$, δ): −135.61--135.83 (2F, m), −136.58--136.79 (2F, m). HRMS for $C_{11}H_{11}F_4NO_6S_2$ [(M−H)$^-$]: calc. 391.9891, found 391.9892.

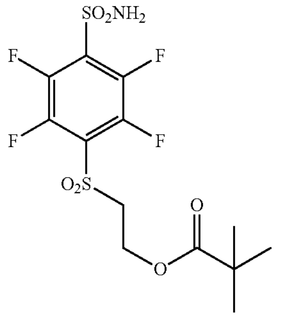 [SMILES: CC(C)(C)C(=O)OCCS(=O)(=O)c1c(F)c(F)c(S(N)(=O)=O)c(F)c1F]

2-((2,3,5,6-tetrafluoro-4-sulfamoylphenyl)sulfonyl)ethyl pivalate (AV22-162)

2,3,5,6-tetrafluoro-4-((2-hydroxyethyl)sulfonyl)benzenesulfonamide (VD10-35-1) (0.050 g; 0.015 mmol), pivalic acid (0.076 g; 0.074 mmol; 5 eq.) and three drops of $H_2SO_4$ (conc.) were dissolved in toluene (10 ml) and refluxed for 30 minutes. The resulting mixture was washed with brine (3×10 ml). The organic phase was dried using anhydrous $Na_2SO_4$ and evaporated under reduced pressure. The product was purified by column chromotography (silica gel, EtOAc/$CHCl_3$ (1:1), Rf=0.62). Yield: 0.018 g; (29%). Mp: 67-68 °C. $^1H$ NMR (400 MHz, DMSO-$d_6$, δ): 1.02 (9H, s, $C(CH_3)_3$), 4.04 (2H, t, J=5.4 Hz, $SO_2CH_2$), 4.42 (2H, t, J=5.5 Hz, $CH_2O$), 8.70 (2H, s, $SO_2NH_2$). $^{13}C$ NMR (100 MHz, DMSO-$d_6$, δ): 26.46 ($C(CH_3)_3$), 38.00 ($C(CH_3)_3$), 56.32 ($SO_2CH_2$), 57.35 ($CH_2O$), 121.12 (C1, t, J($^{19}F$-$^{13}C$)=14.9 Hz), 127.94 (C4, t, J($^{19}F$-$^{13}C$)=15.4 Hz), 143.01 (C2 and C6, dd, $^1J$($^{19}F$-$^{13}C$)=257.3 Hz, $^2J$($^{19}F$-$^{13}C$)=13.4 Hz), 144.35 (C3 and C5, dd, $^1J$($^{19}F$-$^{13}C$)=256.9 Hz, $^2J$($^{19}F$-$^{13}C$)=16.7 Hz), 176.84 (OC(O)). $^{19}F$ NMR (376 MHz, DMSO-$d_6$, δ): −135.72--135.90 (2F, m), −136.46--136.63 (2F, m). HRMS for $C_{13}H_{15}F_4NO_6S_2$ [(M−H)$^-$]: calc. 420.0204, found 420.0202.

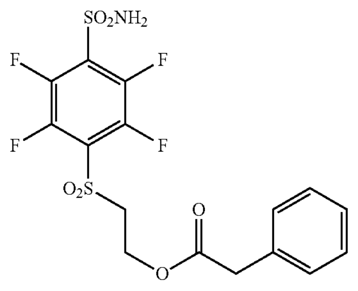 [SMILES: NS(=O)(=O)c1c(F)c(F)c(S(=O)(=O)CCOC(=O)Cc2ccccc2)c(F)c1F]

2-((2,3,5,6-tetrafluoro-4-sulfamoylphenyl)sulfonyl)ethyl 2-phenylacetate (AV21-25)

2,3,5,6-tetrafluoro-4-((2-hydroxyethyl)sulfonyl)benzenesulfonamide (VD10-35-1) (0.041 g; 0.122 mmol; 1 eq.), phenylacetic acid (0.075 g; 0.551 mmol; 5 eq.) and three drops of $H_2SO_4$ (conc.) were dissolved in toluene (15 ml) and refluxed for 1 hour. The resulting mixture was washed with brine (3×10 ml). The organic phase was dried using anhydrous $Na_2SO_4$ and evaporated under reduced pressure. The product was purified by column chromatography (silica gel, EtOAc/$CHCl_3$ (1:1), Rf=0.71). Yield: 0.0282 g; (51%). Mp: 77-79 °C. $^{1}$H NMR (400 MHz, DMSO-$d_6$, δ): 3.49 (2H, s, OC(O)$CH_2$), 4.05 (2H, t, J=5.5 Hz, $SO_2CH_2$), 4.46 (2H, t, J=5.5 Hz, $CH_2O$), 7.19 (2H, d, J=6.9 Hz, phenyl), 7.26 (1H, t, J=7.2 Hz, phenyl), 7.31 (2H, t, J=7.1 Hz, phenyl), 8.69 (2H, s, $SO_2NH_2$). $^{13}$C NMR (100 MHz, DMSO-$d_6$, δ): 40.68 ($COCH_2$), 55.96 ($SO_2CH_2$), 57.55 ($CH_2O$), 121.24 (C1, t, J($^{19}$F-$^{13}$C)=14.8 Hz), 126.95 (C4 of phenyl), 127.90 (C4, t, J($^{19}$F-$^{13}$C)=15.7 Hz), 128.36 (phenyl), 142.96 (C2 and C6, dd, $^{1}$J($^{19}$F-$^{13}$C)=259.0 Hz, $^{2}$J($^{19}$F-$^{13}$C)=17.7 Hz), 144.33 (C3 and C5, dd, $^{1}$J($^{19}$F-$^{13}$C)=254.2 Hz, $^{2}$J($^{19}$F-$^{13}$C)=18.6 Hz), 170.50 (OC(O)). $^{19}$F NMR (376 MHz, DMSO-$d_6$, δ): −135.53-−135.70 (2F, m), −136.43-−136.60 (2F, m). HRMS for $C_{16}H_{13}F_4NO_6S_2$ [(M−H)$^-$]: calc. 454.0048, found 454.0044.

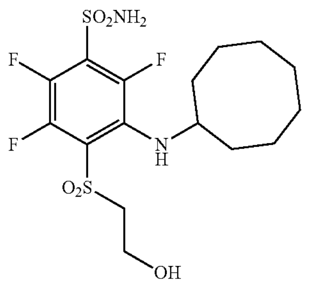 [SMILES: NS(=O)(=O)c1c(F)c(F)c(S(=O)(=O)CCO)c(NC2CCCCCCC2)c1F]

3-(cyclooctylamino)-2,5,6-trifluoro-4-((2-hydroxyethyl)sulfonyl)benzenesulfonamide (VD11-4-2)

3-(cyclooctylamino)-2,5,6-trifluoro-4-((2-hydroxyethyl)sulfonyl)benzenesulfonamide was prepared according to known procedure in literature (Dudutienė, V. et al. *J. Med. Chem.* 57 9435-9446, (2014)). 2,3,5,6-tetrafluoro-4-((2-hydroxyethyl)sulfonyl)benzenesulfonamide (VD10-35-1) (0.549 g 1.63 mmol; 1 eq.) and cyclooctylamine (0.446 ml; 3.26 mmol; 2 eq.) were dissolved in DMSO (2 ml) and left stirring at room temperature overnight. After full starting material conversion reaction mixture was washed with brine (10 ml) and extracted with EtOAc (3×15 ml). The organic phase was dried using anhydrous $Na_2SO_4$ and evaporated under reduced pressure. The product was purified by column chromotography (silica gel, EtOAc/$CHCl_3$ (1:1), Rf=0.52). Yield 0.380 g; (52%). Mp: 90-91 °C (close to the value in the literature (Dudutienė, V. et al. *J. Med. Chem.* 57, 9435-9446 (2014), mp: 89-90 °C).

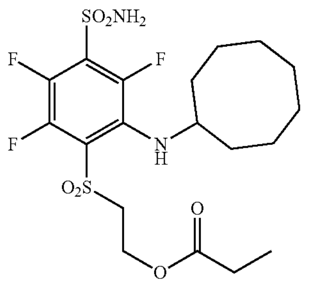 [SMILES: CCC(=O)OCCS(=O)(=O)c1c(F)c(F)c(S(N)(=O)=O)c(F)c1NC1CCCCCCC1]

2-((2-(cyclooctylamino)-3,5,6-trifluoro-4-sulfamoylphenyl)sulfonyl)ethyl propionate (AV21-08)

3-(cyclooctylamino)-2,5,6-trifluoro-4-((2-hydroxyethyl)sulfonyl)benzenesulfonamide (VD11-4-2) (0.100 g; 0.225 mmol), propionic acid (3 ml) and three drops of $H_2SO_4$ (conc.) were dissolved in toluene (25 ml) and refluxed for 3 hours. The resulting mixture was washed with brine (3×10 ml). The organic phase was dried using anhydrous $Na_2SO_4$ and evaporated under reduced pressure. The product was purified by column chromotography (silica gel, EtOAc/$CHCl_3$ (1:1), Rf=0.89) and yellow oil was obtained. Yield: 0.0313 g; (28%). $^{1}$H NMR (400 MHz, $CDCl_3$, δ): 1.06 (3H, t, J=7.6 Hz, $CH_3$), 1.45-1.74 (12H, m, cyclooctane), 1.83-1.92 (2H, m, cyclooctane), 2.17 (2H, q, J=7.6 Hz, $CH_2CH_3$), 3.66 (2H, t, J=5.8 Hz, $SO_2CH_2$), 3.88 (1H, s, CH of cyclooctane), 4.49 (2H, t, J=5.8 Hz, $CH_2O$), 5.55 (2H, s, $SO_2NH_2$), 6.85 (1H, d, J=8.0 Hz, NH). $^{13}$C NMR (100 MHz, $CDCl_3$, δ): 8.88 ($CH_3$), 23.40 (cyclooctane), 25.56 (cyclooctane), 27.19 ($CH_2CH_3$), 27.31 (cyclooctane), 33.06 (cyclooctane), 56.25 (CH of cyclooctane, d, J($^{19}$F-$^{13}$C)=11.7 Hz), 56.58 ($SO_2CH_2$, d, J($^{19}$F-$^{13}$C)=3.9 Hz), 57.28 ($CH_2O$), 115.18 (C1, dd, $^{1}$J($^{19}$F-$^{13}$C)=13.3 Hz, $^{2}$J($^{19}$F-$^{13}$C)=6.5 Hz), 126.63 (C4, dd, $^{1}$J($^{19}$F-$^{13}$C)=16.8 Hz, $^{2}$J($^{19}$F-$^{13}$C)=13.4 Hz), 135.89 (C3, d, J($^{19}$F-$^{13}$C)=12.9 Hz), 136.59 (C6, ddd, $^{1}$J($^{19}$F-$^{13}$C)=248.3 Hz, $^{2}$J ($^{19}$F-$^{13}$C)=17.4 Hz, $^{3}$J($^{19}$F-$^{13}$C)=4.3 Hz), 144.39 (C2, d, $^{1}$J($^{19}$F-$^{13}$C)=253.3 Hz, $^{2}$J($^{19}$F-$^{13}$C)=3.7 Hz), 146.30 (C5, ddd, $^{1}$J($^{19}$F-$^{13}$C)=253.2 Hz, $^{2}$J($^{19}$F-$^{13}$C)=16.5 Hz, $^{3}$J($^{19}$F-$^{13}$C)=5.0 Hz), 173.73 (OC(O)). $^{19}$F NMR (376 MHz, $CDCl_3$, δ): −125.61 (1F, dd, $^{1}$J=12.4 Hz, $^{2}$J=8.9 Hz), −132.79 (1F, dd, $^{1}$J=25.8 Hz, $^{2}$J=12.5 Hz), −151.60 (1F, dd, $^{1}$J=25.8 Hz, $^{2}$J=8.8 Hz). HRMS for $C_{19}H_{27}F_3N_2O_6S_2$ [(M+H)$^+$]: calc. 501.1335, found 501.1339.

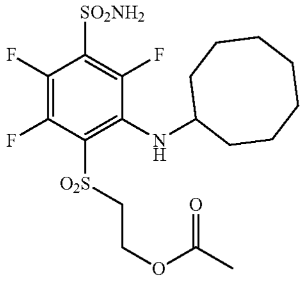 [SMILES: CC(=O)OCCS(=O)(=O)c1c(F)c(F)c(S(N)(=O)=O)c(F)c1NC1CCCCCCC1]

2-((2-(cyclooctylamino)-3,5,6-trifluoro-4-sulfamoylphenyl)sulfonyl)ethyl acetate (AV19-37)

3-(cyclooctylamino)-2,5,6-trifluoro-4-((2-hydroxyethyl)sulfonyl)benzenesulfonamide (VD11-4-2) (0.040 g; 0.090 mmol), acetic acid (1.2 ml) and two drops of $H_2SO_4$ (conc.) were dissolved in toluene (10 ml) and refluxed for 1 hour. The resulting mixture was washed with brine (3×10 ml). The organic phase was dried using anhydrous $Na_2SO_4$ and evaporated under reduced pressure. The product was purified by column chromotography (silica gel, EtOAc/$CHCl_3$ (1:1), Rf=0.78). Yield: 0.0203 g; (46%). Mp: 96 °C. $^{1}$H NMR (400 MHz, $CDCl_3$, δ): 1.45-1.73 (12H, m, cyclooctane), 1.83-1.91 (2H, m, cyclooctane), 1.93 (3H, s, $CH_3$), 3.66 (2H, t, J=5.7 Hz, $SO_2CH_2$), 3.88 (1H, s, CH of cyclooctane), 4.48 (2H, t, J=5.7 Hz, $CH_2O$), 5.65 (2H, s, $SO_2NH_2$), 6.84 (2H, d, J=6.7 Hz, NH). $^{13}$C NMR (100 MHz, $CDCl_3$, δ): 20.46 ($CH_3$), 23.38 (cyclooctane), 25.54 (cyclooctane), 27.31 (cyclooctane), 33.04 (cyclooctane), 56.24 (CH of cyclooctane, d, J ($^{19}$F-$^{13}$C)=11.7 Hz), 56.43 ($SO_2CH_2$, d, J($^{19}$F-$^{13}$C)=4.0 Hz), 57.39 ($CH_2O$), 115.10 (C1, dd, $^{1}$J($^{19}$F-$^{13}$C)=12.7 Hz, $^{2}$J($^{19}$F-$^{13}$C)=5.9 Hz), 126.63 (C4, dd, $^{1}$J($^{19}$F-$^{13}$C)=17.1 Hz, $^{2}$J ($^{19}$F-$^{13}$C)=13.3 Hz), 135.85 (C3, d, J($^{19}$F-$^{13}$C)=13.6 Hz), 136.57 (C6, ddd, $^{1}$J($^{19}$F-$^{13}$C)=248.33 Hz, $^{2}$J($^{19}$F-$^{13}$C)=17.8 Hz, $^{3}$J($^{19}$F-$^{13}$C)=3.9 Hz), 144.36 (C2, d, $^{1}$J($^{19}$F-$^{13}$C)=252.7 Hz), 146.28 (C5, dd, $^{1}$J($^{19}$F-$^{13}$C)=252.8 Hz, $^{2}$J($^{19}$F-$^{13}$C)=15.8 Hz, $^{3}$J($^{19}$F-$^{13}$C)=4.5 Hz), 170.29 (OC(O)). $^{19}$F NMR (376 MHz, $CDCl_3$, δ): −125.63 (1F, dd, $^{1}$J=12.4 Hz, $^{2}$J=8.8 Hz), −132.86 (1F, dd, $^{1}$J=25.7 Hz, $^{2}$J=12.5 Hz), −151.63 (1F, dd, $^{1}$J=25.8 Hz, $^{2}$J=8.8 Hz). HRMS for $C_{18}H_{25}F_3N_2O_6S_2$ [(M+H)$^+$]: calc. 487.1179, found 487.1179.

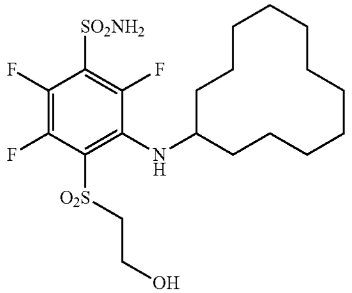 [SMILES: NS(=O)(=O)c1c(F)c(F)c(S(=O)(=O)CCO)c(NC2CCCCCCCCCCC2)c1F]

3-(cyclododecylamino)-2,5,6-trifluoro-4-((2-hydroxyethyl)sulfonyl)benzenesulfonamide (AV19-51)

3-(cyclododecylamino)-2,5,6-trifluoro-4-((2-hydroxyethyl)sulfonyl)benzenesulfonamide was prepared according to known procedure in literature (Dudutienė, V. et al. *ChemMedChem,* 10, 662-687 (2015)). 2,3,5,6-tetrafluoro-4-((2-hydroxyethyl)sulfonyl)benzenesulfonamide (VD10-35-1) (0.300 g 0.89 mmol; 1 eq.) and cyclododecylamine (0.326 g; 1.78 mmol; 2 eq.) were dissolved in DMSO (2 ml) and left stirring at room temperature for 2 hours. After full starting material conversion reaction mixture was washed with brine (10 ml) and extracted with EtOAc (3×15 ml). The organic phase was dried using anhydrous $Na_2SO_4$ and evaporated under reduced pressure. The product was purified by column chromotography (silica gel, EtOAc/$CHCl_3$ (1:1), Rf=0.60). Yield: 0.278 g; (62%). Mp: 143-145 °C (close to the value in the literature (Dudutienė, V. et al. *ChemMedChem,* 10, 662-687 (2015)), mp: 143-144 °C).

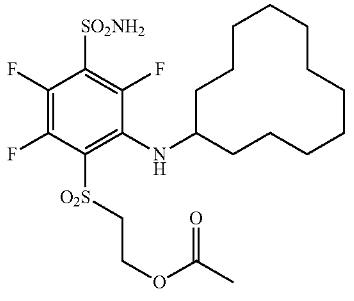 [SMILES: CC(=O)OCCS(=O)(=O)c1c(F)c(F)c(S(N)(=O)=O)c(F)c1NC1CCCCCCCCCCC1]

2-((2-(cyclododecylamino)-3,5,6-trifluoro-4-sulfamoylphenyl)sulfonyl)ethyl acetate (AV21-47)

3-(cyclododecylamino)-2,5,6-trifluoro-4-((2-hydroxyethyl)sulfonyl)benzenesulfonamide (AV19-51) (0.102 g; 0.204 mmol), acetic acid (4 ml) and three drops of $H_2SO_4$ (conc.) were dissolved in toluene (25 ml) and refluxed for 4 hours. The resulting mixture was washed with brine (3×10 ml). The organic phase was dried using anhydrous $Na_2SO_4$ and evaporated under reduced pressure. The product was purified by column chromotography (silica gel, EtOAc/$CHCl_3$ (1:1), Rf=0.86). Yield: 0.052 g; (47%). Mp: 138-140 °C. $^{1}$H NMR (400 MHz, DMSO-$d_6$, δ): 1.21-1.46 (20H, m, cyclododecane), 1.55-1.65 (2H, m, cyclododecane), 1.81 (3H, s, OC(O)$CH_3$), 3.78 (1H, s, CH of cyclododecane), 3.92 (2H, t, J=4.9 Hz, $SO_2CH_2$), 4.36 (2H, t, J=4.9 Hz, $CH_2O$), 6.52 (1H, d, J=8.6 Hz, NH), 8.38 (2H, s, $SO_2NH_2$). $^{13}$C NMR (100 MHz, DMSO-$d_6$, δ): 20.04 ($CH_3$), 20.45 (cyclododecane), 22.60 (cyclododecane), 22.71 (cyclododecane), 23.73 (cyclododecane), 23.89 (cyclododecane), 30.08 (cyclododecane), 52.84 (CH of cyclododecane, d, J=11.6 Hz), 55.66 ($SO_2CH_2$, d, J=2.3 Hz), 57.65 ($CH_2O$), 115.34 (C1, dd, $^{1}$J($^{19}$F-$^{13}$C)=13.2 Hz, $^{2}$J($^{19}$F-$^{13}$C)=5.1 Hz), 127.71 (C4, dd, $^{1}$J($^{19}$F-$^{13}$C)=18.1 Hz, $^{2}$J($^{19}$F-$^{13}$C)=13.9 Hz), 135.13 (C3, d, $^{1}$J($^{19}$F-$^{13}$C)=15.3 Hz), 136.67 (C6, d, $^{1}$J($^{19}$F-$^{13}$C)=253.6 Hz), 143.95 (C2, d, $^{1}$J($^{19}$F-$^{13}$C)=252.9 Hz), 145.58 (C5, dd, $^{1}$J($^{19}$F-$^{13}$C)=246.4 Hz, $^{2}$J($^{19}$F-$^{13}$C)=13.7 Hz), 169.54 (OC(O)). $^{19}$F NMR (376 MHz, DMSO-$d_6$,): −124.88 (1F, s), −134.22 (1F, dd, $^{1}$J=26.8 Hz, $^{2}$J=12.5 Hz), −150.76 (1F, dd, $^{1}$J=26.8 Hz, $^{2}$J=6.7 Hz). HRMS for $C_{22}H_{33}F_3N_2O_6S_2$ [(M+H)$^+$]: calc. 543.1805, found 543.1803.

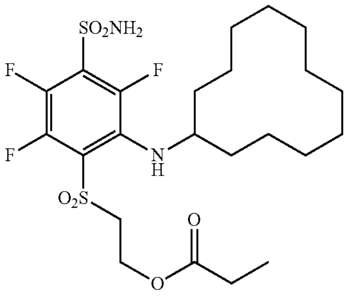 [SMILES: CCC(=O)OCCS(=O)(=O)c1c(F)c(F)c(S(N)(=O)=O)c(F)c1NC1CCCCCCCCCCC1]

2-((2-(cyclododecylamino)-3,5,6-trifluoro-4-sulfamoylphenyl)sulfonyl)ethyl propionate (AV22-132)

3-(cyclododecylamino)-2,5,6-trifluor-4-((2-hydroxyethyl)sulfonyl)benzenesulfonamide (AV19-51) (0.0377 g; 0.075 mmol), propionic acid (2 ml) and three drops of $H_2SO_4$ (conc.) were dissolved in toluene (10 ml) and refluxed for 1 hour. The resulting mixture was washed with brine (2×5 ml). The organic phase was dried using anhydrous $Na_2SO_4$ and evaporated under reduced pressure. The product was purified by column chromotography (silica gel, $CHCl_3$, Rf=0.20). Yield: 0.0248 g; (59%). Mp: 110-112 °C. $^1$H NMR (400 MHz, DMSO-$d_6$, δ): 0.91 (3H, t, J=7.5 Hz, $CH_3$), 1.23-1.44 (20H, m, cyclododecane), 1.54-1.64 (2H, m, cyclododecane), 2.05 (2H, q, J=7.6 Hz, $CH_2CH_3$), 3.78 (1H, s, CH of cyclododecane), 3.94 (2H, t, J=5.2 Hz, $SO_2CH_2$), 4.37 (2H, t, J=5.0 Hz, $CH_2O$), 6.52 (1H, d, J=8.2 Hz, NH), 8.40 (2H, s, $SO_2NH_2$). $^{13}$C NMR (100 MHz, DMSO-$d_6$, δ): 8.56 ($CH_3$), 20.44 (cyclododecane), 22.58 (cyclododecane), 22.70 (cyclododecane), 23.71 (cyclododecane), 23.87 (cyclododecane), 26.36 ($CH_2CH_3$), 30.08 (cyclododecane), 52.82 (CH of cyclododecane, d, J=11.6 Hz), 55.76 ($SO_2CH_2$), 57.59 ($CH_2O$), 115.32 (C1, t, J($^{19}$F-$^{13}$C)=7.0 Hz), 127.67 (C4, t, J($^{19}$F-$^{13}$C)=14.2 Hz), 135.11 (dd, $^1$J ($^{19}$F-$^{13}$C)=13.9 Hz, $^2$J($^{19}$F-$^{13}$C)=2.4 Hz), 136.65 (C6, d, $^1$J($^{19}$F-$^{13}$C)=252.8 Hz), 143.98 (C2, d, $^1$J($^{19}$F-$^{13}$C) 253.0 Hz,), 145.56 (C5, dd, $^1$J($^{19}$F-$^{13}$C)=249.8 Hz, $^2$J($^{19}$F-$^{13}$C)=15.4 Hz), 172.82 (OC(O)). $^{19}$F NMR (376 MHz, DMSO-$d_6$, δ): −124.86 (1F, s), −134.21 (1F, dd, $^1$J=26.9 Hz, $^2$J=12.4 Hz), −150.79 (1F, dd, $^1$J=26.9 Hz, $^2$J=6.6 Hz). HRMS for $C_{23}H_{35}F_3N_2O_6S_2$ [(M+H)$^+$]: calc. 557.1961, found 557.1966.

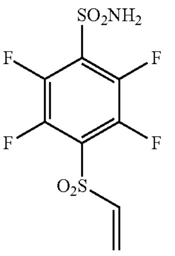 [SMILES: C=CS(=O)(=O)c1c(F)c(F)c(S(N)(=O)=O)c(F)c1F]

2,3,5,6-tetrafluoro-4-(vinylsulfonyl)benzenesulfonamide (AV22-48)

2,3,5,6-tetrafluoro-4-((2-hydroxyethyl)sulfonyl)benzenesulfonamide (0.200 g; 0.592 mmol; 1 eq.), thionyl chloride (0.064 ml; 0.85 mmol; 1.5 eq.), $Et_3N$ (0.006 ml; 0.43 mmol; 0.75 eq.) were dissolved in MeCN (2 ml) and left stirring at room temperature for 52 hours. The resulting mixture was washed with brine (3×10 ml). The organic phase was dried using anhydrous $Na_2SO_4$ and evaporated under reduced pressure. The product was purified by column chromotography (silica gel, EtOAc/$CHCl_3$ (1:1), Rf=0.64). Yield: 0.173 g; (92%). Mp: 174-176 °C. $^1$H NMR (400 MHz, DMSO-$d_6$, δ): 6.54 (1H, d, J=17.0 Hz, $CH_2$), 6.57 (1H, d, J=23.6 Hz, $CH_2$), 7.36 (1H, dd, $^1$J=16.3 Hz, $^2$J=9.8 Hz, CH), 8.63 (2H, s, $SO_2NH_2$). $^{13}$C NMR (100 MHz, DMSO-$d_6$, δ): 121.79 (C1, t, J($^{19}$F-$^{13}$C)=14.2 Hz), 128.17 (C4, t, J($^{19}$F-$^{13}$C)=15.7 Hz), 133.34 ($CH_2$), 138.12 (CH), 143.45 (C3 and C5, dd, $^1$J($^{19}$F-$^{13}$C)=259.0 Hz, $^2$J($^{19}$F-$^{13}$C)=11.1 Hz) 144.49 (C2 and C6, dd, $^1$J($^{19}$F-$^{13}$C)=256.0 Hz, $^2$J($^{19}$F-$^{13}$C)=14.8 Hz). $^{19}$F NMR (376 MHz, DMSO-$d_6$, δ): −135.89--136.11 (2F, m), −136.43--136.72 (2F, m). HRMS for $C_8H_5F_4NO_4S_2$ [(M−H)$^-$]: calc. 317.9523, found 317.9524.

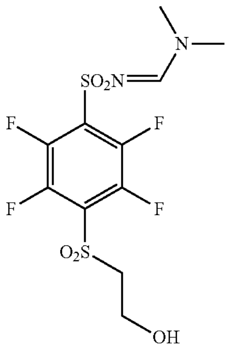

N,N-dimethyl-N'-((2,3,5,6-tetrafluoro-4-((2-hydroxyethyl)sulfonyl)phenyl)sulfonyl)formimidamide (AV21-56)

2,3,5,6-tetrafluoro-4-((2-hydroxyethyl)sulfonyl)benzenesulfonamide (0.160 g; 0.047 mmol) and N,N-dimethylformamide dimethyl acetal (0.076 g; 0.074 mmol; 5 eq.) were dissolved in acetonitrile (10 ml) and left stirring at room temperature for 1 hour. The solvent was evaporated under reduced pressure and the product was purified by column chromotography (silica gel, EtOAc, Rf=0.65). Yield: 0.155 g; (83%). Mp: 188-189 °C. $^1$H NMR (400 MHz, DMSO-$d_6$, δ): 2.99 (3H, s, $NCH_3$), 3.23 (3H, s, $NCH_3$), 3.71 (2H, t, J=5.3 Hz, $SO_2CH_2$), 3.85 (2H, q, J=5.3 Hz, $CH_2OH$), 4.98 (1H, t, J=5.2 Hz, OH), 8.30 (1H, s, NCHN). $^{13}$C NMR (100 MHz, DMSO-$d_6$, δ): 35.64 ($NCH_3$), 41.36 ($NCH_3$), 55.07 ($SO_2CH_2$), 59.53 ($CH_2OH$), 122.46 (C1, t, J($^{19}$F-$^{13}$C)=15.1 Hz), 126.45 (C4, t, J($^{19}$F-$^{13}$C)=15.2 Hz), 143.00 (C2 and C6, dd, $^1$J($^{19}$F-$^{13}$C)=253.7 Hz, $^2$J ($^{19}$F-$^{13}$C)=17.8 Hz), 144.23 (C3 and C5, dd, $^1$J($^{19}$F-$^{13}$C)=252.2 Hz, $^2$J($^{19}$F-$^{13}$C)=16.3 Hz), 160.93 (NCHN). $^{19}$F NMR (376 MHz, DMSO-$d_6$, δ): −136.20--136.38 (2F, m), −136.72--136.91 (2F, m). HRMS for $C_{11}H_{12}F_4N_2O_5S_2$ [(M+H)$^+$]: calc. 393.0197, found 393.0199.

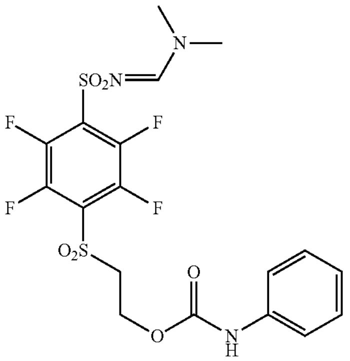

2-((4-(N-((dimethylamino)methylene)sulfamoyl)-2,3,5,6-tetrafluorophenyl)sulfonyl)ethyl phenylcarbamate (AV22-137)

N,N-dimethyl-N'-((2,3,5,6-tetrafluoro-4-((2-hydroxyethyl)sulfonyl)phenyl)sulfonyl)formimidamide (0.068 g; 0.17 mmol; 1 eq.) and phenyl isocyanate (0.028 ml; 0.26 mmol; 1.5 eq.) were dissolved in toluene (10 ml) and refluxed at boiling point for 14 hours. Additional phenyl isocyanate portions (0.057 ml; 0.052 mmol; 3 eq.) were added after 2 hours and 7 hours respectively. The solvent was evaporated under reduced pressure and the product was purified by column chromatography (silica gel, EtOAc/$CHCl_3$ (1:1), Rf=0.43). Yield: 0.072 g; (81%). Mp: 177-178 °C. $^1$H NMR (400 MHz, DMSO-$d_6$, δ): 2.96 (3H, s, $NCH_3$), 3.22 (3H, s, $NCH_3$), 4.04 (2H, t, J=5.3 Hz, $SO_2CH_2$), 4.51 (2H, t, J=5.4 Hz, $CH_2O$), 7.00 (1H, t, J=7.3 Hz, CH (C4) of phenyl), 7.27 (2H, t, J=7.8 Hz, CH (C3 and C5) of phenyl), 7.39 (2H, d, J=7.6 Hz, CH (C2 and C6) of phenyl), 8.27 (1H, s, NCHN), 9.62 (1H, s, OC(O)NH). $^{13}$C NMR (100 MHz, DMSO-$d_6$, δ): 35.61 ($NCH_3$), 41.34 ($NCH_3$), 56.36 ($SO_2CH_2$), 57.38 ($CH_2O$), 118.54 (C4 of phenyl), 121.10 (C1, t, J($^{19}$F-$^{13}$C)=14.9 Hz), 122.75 (C3 and C5 of phenyl), 126.95 (C4, t, J($^{19}$F-$^{13}$C)=15.1 Hz), 128.70 (C2 and C6 of phenyl), 138.54 (C1 of phenyl), 143.29 (C2 and C6, dd, $^1$J($^{19}$F-$^{13}$C)=262.1 Hz, $^2$J($^{19}$F-$^{13}$C)=22.0 Hz), 144.25 (C5 and C3, dd, $^1$J($^{19}$F-$^{13}$C)=247.2 Hz, $^2$J($^{19}$F-$^{13}$C)=13.0 Hz), 152.64 (OC(O)NH), 160.89 (NCHN). $^{19}$F NMR (376 MHz, DMSO-$d_6$, δ): −135.99-−136.16 (2F, m), −136.28-−136.47 (2F, m). HRMS for $C_{18}H_{17}F_4N_3O_6S_2$ [(M+H)$^+$]: calc. 512.0568, found 512.0571.

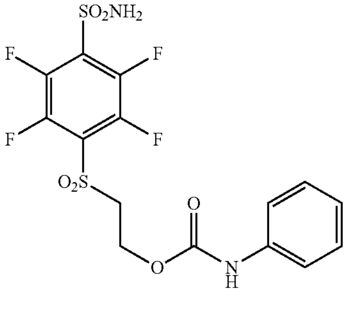 [SMILES: NS(=O)(=O)c1c(F)c(F)c(S(=O)(=O)CCOC(=O)Nc2ccccc2)c(F)c1F]

2-((2,3,5,6-tetrafluoro-4-sulfamoylphenyl)sulfonyl)ethyl phenylcarbamate (AV22-138-1)

2-((4-(N-((dimethylamino)methylene)sulfamoyl)-2,3,5,6-tetrafluorophenyl)sulfonyl)ethyl phenylcarbamate (0.030 g; 0.059 mmol; 1 eq.) and three drops of HCl (conc.) were dissolved in toluene (3 ml) and refluxed at boiling point for 18 hours. After 5 hours additional 10 drops of HCl (conc.) were added. The solvent was evaporated under reduced pressure and the product was purified by column chromatography (silica gel, EtOAc/$CHCl_3$ (1:1), Rf=0.59). Yield: 0.007 g; (26%). Mp: 64-66 °C. $^1$H NMR (400 MHz, DMSO-$d_6$, δ): 4.06 (2H, t, J=5.4 Hz, $SO_2CH_2$), 4.52 (2H, t, J=5.5 Hz, $CH_2O$), 7.00 (1H, t, J=7.3 Hz, CH (C4) of phenyl), 7.26 (2H, t, J=7.9 Hz, (C3 and C5) of phenyl), 7.41 (2H, d, J=7.9 Hz, CH (C2 and C6) of phenyl), 8.60 (2H, s, $SO_2NH_2$), 9.65 (1H, s, OC(O)NH). $^{19}$F NMR (376 MHz, DMSO-$d_6$, δ): −136.18-−136.49 (4F, m). HRMS for $C_{15}H_{12}F_4N_2O_6S_2$ [(M−H)$^-$]: calc. 455.0000, found 455.0001.

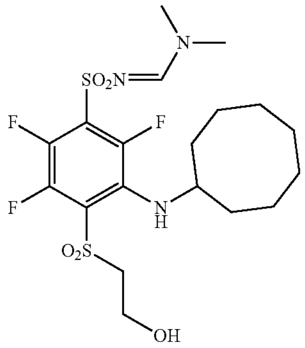

N'-((3-(cyclooctylamino)-2,5,6-trifluoro-4-((2-hydroxyethyl)sulfonyl)phenyl)sulfonyl)-N,N-dimethylformimidamide (AV22-141)

N,N-dimethyl-N'-((2,3,5,6-tetrafluoro-4-((2-hydroxyethyl)sulfonyl)phenyl)sulfonyl)formimidamide (0.100 g; 0.25 mmol; 1 eq.) and cyclooctylamine (0.070 ml; 0.51 mmol; 2 eq.) were dissolved in DMSO (1 ml) and left stirring at room temperature for 1.5 hours. The reaction mixture was washed with brine (5 ml) and extracted using EtOAc (3×10 ml). The collected organic phase was dried using anhydrous $Na_2SO_4$ and evaporated under reduced pressure. The product was purified by column chromatography (silica gel, EtOAc, Rf=0.64) and yellow oil was obtained. Yield: 0.062 g; (49%). $^1$H NMR (400 MHz, DMSO-$d_6$, δ): 1.40-1.70 (12H, m, cyclooctane), 1.76-1.87 (2H, m, cyclooctane), 2.97 (3H, s, $NCH_3$), 3.21 (3H, s, $NCH_3$), 3.64 (2H, t, J=5.4 Hz, $SO_2CH_2$), 3.73 (1H, br.s, CH of cyclooctane), 3.81 (2H, q, J=5.4 Hz, $CH_2OH$), 4.98 (1H, t, J=5.2 Hz, OH), 6.60 (1H, d, J=8.2 Hz, NH), 8.28 (1H, s, NCHN). $^{13}$C NMR (100 MHz, DMSO-$d_6$, δ): 22.89 (cyclooctane), 25.11 (cyclooctane), 26.65 (cyclooctane), 32.27 (cyclooctane), 35.48 ($NCH_3$), 41.20 ($NCH_3$), 55.02 ($CH_2OH$), 55.31 (CH of cyclooctane, d, J($^{19}$F-$^{13}$C)=11.1 Hz), 59.52 ($SO_2CH_2$, d, J($^{19}$F-$^{13}$C)=2.5 Hz), 116.70 (C1, dd, $^1$J($^{19}$F-$^{13}$C)=12.8 Hz, $^2$J($^{19}$F-$^{13}$C)=5.5 Hz), 126.05 (C4, dd, $^1$J($^{19}$F-$^{13}$C)=18.2 Hz, $^2$J($^{19}$F-$^{13}$C)=13.9 Hz), 134.49 (C3, d, J($^{19}$F-$^{13}$C)=16.1 Hz), 136.97 (C6, d, J($^{19}$F-$^{13}$C)=246.7 Hz), 144.26 (C2, d, $^1$J($^{19}$F-$^{13}$C)=252.5 Hz), 145.62 (C5, dd, $^1$J($^{19}$F-$^{13}$C)=246.0 Hz, $^2$J ($^{19}$F-$^{13}$C)=12.4 Hz), 160.75 (NCHN). $^{19}$F NMR (376 MHz, DMSO-$d_6$, δ): −124.67 (1F, br.s), −134.26 (1F, dd, $^1$J=27.3 Hz, $^2$J=12.2 Hz), −150.64

(1F, dd, $^1J$=27.3 Hz, $^2J$=6.7 Hz). HRMS for $C_{19}H_{28}F_3N_3O_5S_2$ [$(M+H)^+$]: calc. 500.1495, found 500.1493.

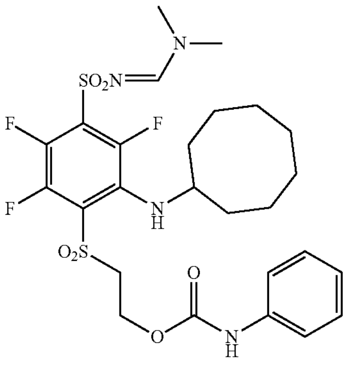

2-((2-(cyclooctylamino)-4-(N-((dimethylamino) methylene)sulfamoyl)-3,5,6-trifluorophenyl)sulfonyl)ethyl phenylcarbamate (AV22-143)

N'-((3-(cyclooctylamino)-2,5,6-trifluoro-4-((2-hydroxyethyl)sulfonyl)phenyl)sulfonyl)-N, N-dimethylformimidamide (0.038 g; 0.08 mmol; 1 eq.) and phenyl isocyanate (0.025 ml; 0.23 mmol; 3 eq.) were dissolved in toluene (7 ml) and refluxed at boiling point for 28 hours. Additional phenyl isocyanate portions (0.025 ml; 0.023 mmol; 3 eq.) were added after 10 hours and 24 hours respectively. The solvent was evaporated under reduced pressure and the product was purified by column chromatography (silica gel, EtOAc/$CHCl_3$ (1:1), Rf=0.65). Yield: 0.018 g; (38%). Mp: 177-178 °C. $^1H$ NMR (400 MHz, DMSO-$d_6$, δ): 1.33-1.63 (12H, m, cyclooctane), 1.71-1.82 (2H, m, cyclooctane), 2.95 (3H, s, $NCH_3$), 3.20 (3H, s, $NCH_3$), 3.69 (1H, br.s, CH of cyclooctane), 3.95 (2H, t, J=5.0 Hz, $SO_2CH_2$), 4.46 (2H, t, J=5.2 Hz, $CH_2O$), 6.58 (1H, d, J=8.2 Hz, $NHCH(CH_2)_2$), 6.99 (1H, t, J=7.3 Hz, CH (C4) of phenyl), 7.26 (2H, t, J=7.8 Hz, CH (C3 and C5) of phenyl), 7.42 (2H, d, J=6.6 Hz, CH (C2 and C6) of phenyl), 8.27 (1H, s, NCHN), 9.66 (1H, s, OC(O)NH). $^{13}C$ NMR (100 MHz, DMSO-$d_6$, δ): 22.83 (cyclooctane), 25.03 (cyclooctane), 26.54 (cyclooctane), 32.31 (cyclooctane), 35.46 ($NCH_3$), 41.20 ($NCH_3$), 55.27 (CH of cyclooctane, d, J=11.3 Hz), 56.14 ($SO_2CH_2$, d, J=2.4 Hz), 57.50 ($CH_2O$), 115.03 (C1, dd, $^1J$ ($^{19}F$-$^{13}C$)=13.2 Hz, $^2J$($^{19}F$-$^{13}C$)=5.9 Hz), 118.48 (C4 of phenyl), 122.64 (C3 and C5 of phenyl), 126.57 (C4, dd, $^1J$($^{19}F$-$^{13}C$)=18.2 Hz, $^2J$($^{19}F$-$^{13}C$)=14.1 Hz), 128.62 (C2 and C6 of phenyl), 134.55 (C3, d, J($^{19}F$-$^{13}C$)=14.5 Hz), 137.09 (C6, ddd, $^1J$($^{19}F$-$^{13}C$)=241.5 Hz, $^2J$ ($^{19}F$-$^{13}C$)=17.6 Hz, $^3J$($^{19}F$-$^{13}C$)=5.0 Hz), 138.68 (C1 of phenyl), 144.29 (C2, dd, $^1J$ ($^{19}F$-$^{13}C$)=253.2 Hz, $^2J$($^{19}F$-$^{13}C$)=21.3 Hz), 145.66 (C5, ddd, $^1J$($^{19}F$-$^{13}C$)=250.5 Hz, $^2J$ ($^{19}F$-$^{13}C$)=17.2 Hz, $^3J$($^{19}F$-$^{13}C$)=4.0 Hz), 152.75 (OC(O) NH), 160.76 (NCHN). $^{19}F$ NMR (376 MHz, DMSO-$d_6$, δ): −124.61 (1F, s), −134.25 (1F, dd, $^1J$=27.4 Hz, $^2J$=12.3 Hz), 150.25 (1F, dd, $^1J$=27.7 Hz, $^2J$=6.7 Hz). HRMS for $C_{26}H_{33}F_3N_4O_6S_2$ [$(M-H)^-$]: calc. 617.1721, found 617.1723.

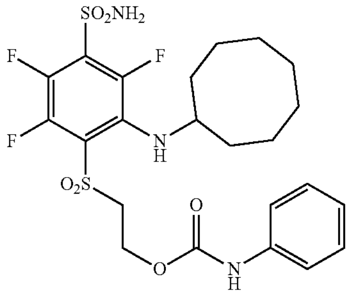 [SMILES: NS(=O)(=O)c1c(F)c(F)c(S(=O)(=O)CCOC(=O)Nc2ccccc2)c(NC2CCCCCCC2)c1F]

2-((2-(cyclooctylamino)-3,5,6-trifluoro-4-sulfamoylphenyl)sulfonyl)ethyl phenylcarbamate (AV22-149)

2-((2-(cyclooctylamino)-4-(N-((dimethylamino)methylene)sulfamoyl)-3,5,6-trifluorophenyl)sulfonyl)ethyl phenylcarbamate (0.015 g; 0.024; 1 eq.) and three drops of HCl (conc.) were dissolved in MeOH (3 ml) and refluxed at boiling point for 29 hours. The solvent was evaporated under reduced pressure and the product was purified by column chromatography (silica gel, EtOAc/$CHCl_3$ (1:1), Rf=0.88). Yield: 0.004 g; (29%). Mp: 158-160 °C. $^1H$ NMR (400 MHz, DMSO-$d_6$, δ): 1.36-1.63 (12H, m, cyclooctane), 1.75-1.85 (2H, m, cyclooctane), 3.72 (1H, br.s, CH of cyclooctane), 3.97 (2H, t, J=5.3 Hz, $SO_2CH_2$), 4.46 (2H, t, J=5.4 Hz, $CH_2O$), 6.62 (1H, d, J=8.3 Hz, $NHCH(CH_2)_2$), 6.99 (1H, t, J=7.3 Hz, C4 of phenyl), 7.26 (2H, t, J=7.8 Hz, C3 and C5 of phenyl), 7.43 (2H, d, J=8.0 Hz, C2 and C6 of phenyl), 8.32 (2H, s, $SO_2NH_2$), 9.67 (1H, s, OC(O)NH). $^{19}F$ NMR (376 MHz, DMSO-$d_6$, δ): −124.89 (1F, s), −134.36 (1F, dd, $^1J$=27.0 Hz, $^2J$=12.2 Hz), −150.47 (1F, dd, $^1J$=27.0 Hz, $^2J$=6.4 Hz). HRMS for $C_{23}H_{28}F_3N_3O_6S_2$ [$(M+H)^+$]: calc. 564.1444, found 564.1444.

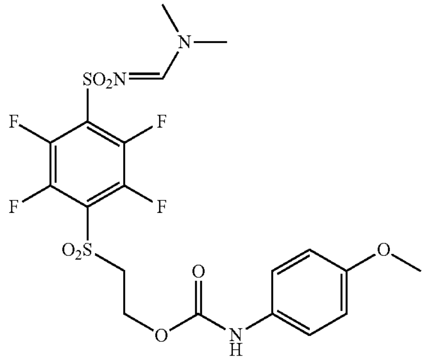

2-((4-(N-((dimethylamino)methylene)sulfamoyl)-2, 3,5,6-tetrafluorophenyl)sulfonyl)ethyl(4-methoxyphenyl)carbamate (AV22-166)

N,N-dimethyl-N'-((2,3,5,6-tetrafluoro-4-((2-hydroxyethyl)sulfonyl)phenyl)sulfonyl)formimidamide (0.050 g; 0.13 mmol; 1 eq.), 4-methoxyphenyl isocyanate (0.025 ml; 0.19 mmol; 1.5 eq.) and dibutyltin dilaurate (0.015 ml; 0.026 mmol; 0.2 eq.) were dissolved in acetonitrile (3 ml). The mixture was stirred at room temperature for 5 days. Additional 4-methoxyphenyl isocyanate portion (0.025 ml; 0.19 mmol; 1.5 eq.) was added after 2 days. The solvent was evaporated under reduced pressure and the product was purified by column chromatography (silica gel, EtOAc/$CHCl_3$ (1:1), Rf=0.41). Yield: 0.008 g; (12%). Mp: 167-168 °C. $^1H$ NMR (400 MHz, DMSO-$d_6$, δ): 2.96 (3H, s, $NCH_3$), 3.21 (3H, s, $NCH_3$), 3.70 (3H, s, $OCH_3$), 4.03 (2H, t, J=5.4 Hz, $SO_2CH_2$), 4.49 (2H, t, J=5.3 Hz, $CH_2O$), 6.85 (2H, d, J=8.8 Hz, C2 and C6 of phenyl), 7.28 (2H, d, J=7.2 Hz, C3 and C6 of phenyl), 8.27 (1H, s, NCHN), 9.41 (1H, s, OC(O)NH). $^{13}C$ NMR (100 MHz, DMSO-$d_6$, δ): 35.58 ($NCH_3$), 41.34 ($NCH_3$), 55.14 ($OCH_3$), 56.40 ($SO_2CH_2$), 57.31 ($CH_2O$), 113.91 (C3 and C5 of phenyl), 120.25 (C2 and C6 of phenyl), 121.13 (C1, t, J=14.7 Hz), 126.91 (C4), 128.63 (C1 of phenyl), 131.52 (C4 of phenyl), 143.34 (C2 and C6, dd, $^1J(^{19}F-^{13}C)$=250.0 Hz, $^2J(^{19}F-^{13}C)$=11.2 Hz), 144.16 (C3 and C5, dd, $^1J(^{19}F-^{13}C)$=242.7 Hz, $^2J(^{19}F-^{13}C)$=10.3 Hz), 152.79 (OC(O)NH), 155.03 (C4 of phenyl), 160.90 (NCHN). $^{19}F$ NMR (376 MHz, DMSO-$d_6$, δ): −135.95–−136.16 (2F, m), −136.30–−136.55 (2F, m). HRMS for $C_{19}H_{19}F_4N_3O_7S_2$ [(M+Na)$^+$]: calc. 564.0493, found 564.0501.

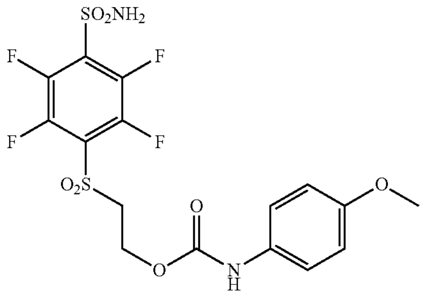 [SMILES: COc1ccc(NC(=O)OCCS(=O)(=O)c2c(F)c(F)c(S(N)(=O)=O)c(F)c2F)cc1]

2-((2,3,5,6-tetrafluoro-4-sulfamoylphenyl)sulfonyl) ethyl(4-methoxyphenyl)carbamate (AV23-04)

2-((4-(N-((dimethylamino)methylene)sulfamoyl)-2,3,5,6-tetrafluorophenyl)sulfonyl)ethyl (4-methoxyphenyl)carbamate (0.006 g; 0.011 mmol; 1 eq.) and three drops of HCl (conc.) were dissolved in MeOH (3 ml) and refluxed for 31 hours. The solvent was evaporated under reduced pressure and the product was purified by column chromatography (silica gel, EtOAc/$CHCl_3$, (1:1), Rf=0.57). Yield: 0.002 g; (37%). Mp: 188-189 °C. $^1H$ NMR (400 MHz, DMSO-$d_6$, δ): 3.70 (3H, s, $OCH_3$), 4.05 (2H, t, J=5.4 Hz, $SO_2CH_2$), 4.49 (2H, t, J=5.4 Hz, $CH_2O$), 6.85 (2H, d, J=8.9 Hz, phenyl), 7.30 (2H, d, J=7.5 Hz, phenyl), 8.61 (2H, s, $SO_2NH_2$), 9.45 (1H, s, OC(O)NH). $^{19}F$ NMR (376 MHz, DMSO-$d_6$, δ): −136.22–−136.49 (4F, m). HRMS for $C_{16}H_{14}F_4N_2O_7S_2$ [(M−H)$^-$]: calc. 485.0106, found 485.0105.

Evaluation of the Binding and Inhibition Properties of Target Compounds

Compound Binding to CA Isozymes

The interaction of synthesized fluorinated compounds with catalytically active recombinant human CA isozymes was tested by fluorescent thermal shift assay (FTSA). An assay is based on the protein thermal stabilization effect by the compound. Compounds that bind to the protein shift the unfolding transition toward higher temperature. The protein melting temperature ($T_m$) shift depends on the compound concentration and binding strength. FTSA experiments were performed as previously described (Zubrienė, A. et al. *ChemMedChem,* 12(2), 161-176 (2017)). The apparent dissociation constant ($K_{d\_app}$) is determined by analyzing ligand dosing curves as described in Gedgaudas, M. et al. *Drug Discovery Today,* 27 (8), 2076-2079 (2022).

Para-substituted compounds bind CA isozyme I (CAI) with the highest affinity; the $K_d$s are in the range 0.0024-0.0084 nM, while substitution with cyclooctyl or cyclododecyl group at meta position decreased affinity by more than 1000 fold (Table 1). In contrast, cancer-related CAIX isozyme binds para-substituted compounds with ten times lower affinity than meta-substituted compounds; para, meta-substituted fluorinated benzenesulfonamides possess extremely high picomolar affinities ($K_d$s 0.0022-0.0091 nM) and are selective for this isozyme.

Most para-substituted compounds bound stronger to CAIII, CAVA, CAVB than para, meta-substituted compounds. CAXII, CAXIII and CAXIV bind all compounds with low nanomolar affinity.

Compound AV19-36 which has S instead of $SO_2$ in the para position and therefore cannot form a covalent bond with nucleophilic amino acids, bound all tested CAs with at least 60 to 1300 fold lower affinity than the similar compound AV21-03-2.

FIG. 1 shows the representative binding data of CAIX with covalent compounds by FTSA and isothermal titration calorimetry (ITC). The binding of AV21-47 to CAIX is very tight with $K_{d,app}$ 2.5 pM (FIG. 1B). The ITC curve of AV19-37 binding to CAIX shows that compound binding stoichiometry is near 1, which corresponds to one molecule of AV19-37 bound in the active site of CAIX (FIG. 1D).

Irreversible Enzyme Inactivation

To determine whether the mechanism of compound binding involves covalent modification of the enzymes, we measured the enzymatic activity of CAIX isozyme in the absence and presence of the compound before and after dialysis. 1.5 μM CAIX was incubated with 15 μM of compound AV19-37 (covalent-binding ligand) and 100 μM AV19-36 (non-covalent-binding ligand) for two hours. The solution of CAIX without a trial compound and the CAIX-compound complexes were then dialyzed in 25 mM Tris buffer solution (pH=7) containing 50 mM NaCl. $CO_2$ hydration velocities were measured by recording absorbance of phenol red (final concentration 50 μM) at 557 nm by using Applied Photophysics SX.18 MV-R stopped-flow spectrometer. Experiments were performed at 25 °C using 25 mM Hepes containing 50 mM NaCl, pH 7.5.

Figure 2:
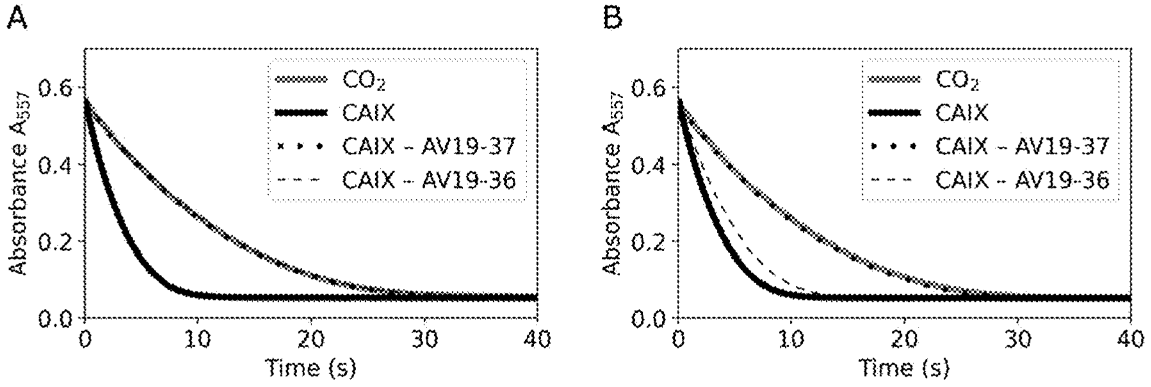
FIG. 2A, B shows CAIX-catalyzed $CO_2$ hydration reaction in the absence and presence of AV19-37 and AV19-36 measured by stopped-flow method. A—CAIX incubated for 2 hours with compounds and the $CO_2$ hydration was measured. B—CAIX was incubated for 2 hours with the compound and then the complex was dialyzed for 32 hours in Tris buffer (pH 7.0). Black curves represent CAIX catalyzed $CO_2$ hydration reaction. Grey curves are spontaneous $CO_2$ hydration without the CA enzyme. The dotted and dashed curves are a $CO_2$ hydration reaction catalyzed by CAIX in the presence of the compound AV19-37 or AV19-36, respectively.

CAIX lost its catalytic activity after 2 hours of incubation with AV19-37 (FIG. 2A), and the activity was not restored after 32 hours of dialysis (FIG. 2B). Whereas CAIX incubated with AV19-36, partially restored its catalytic activity after dialysis, showing the reversible binding of this compound towards CAIX.

Figure 3:
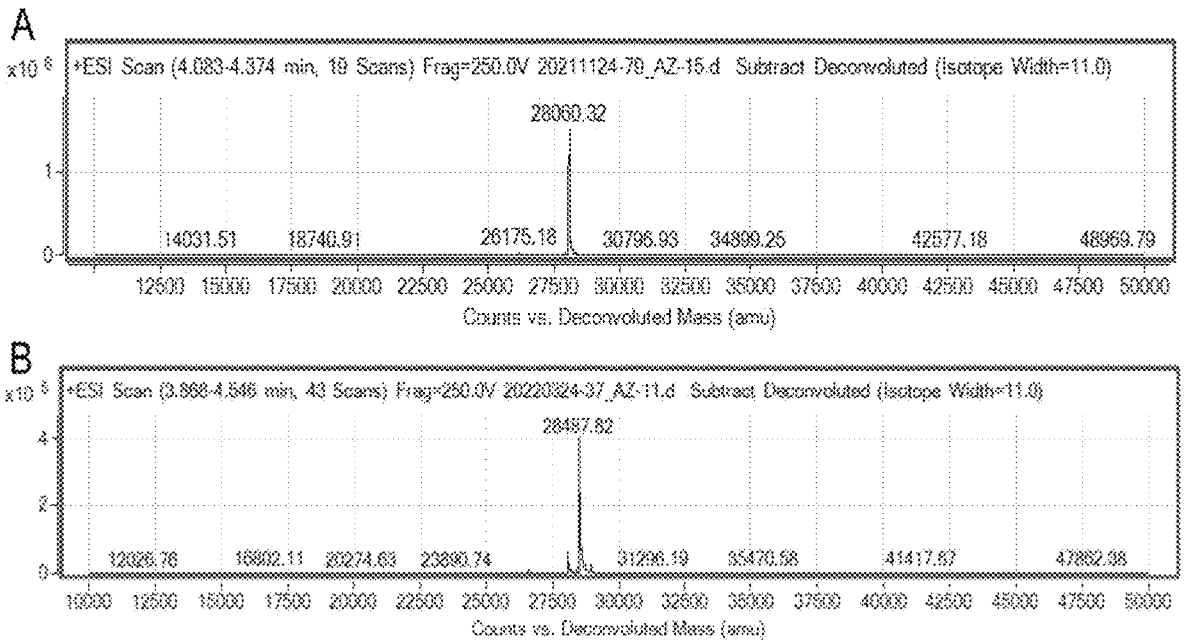
FIG. 3A., B shows mass spectra of native CAIX and CAIX-AV19-37 complex. A—MS spectra of native CAIX corresponds to molecular mass of the protein equal to 28060.32. B—spectra of CAIX incubated with AV19-37 (protein/ligand molar ratio 1:2). The difference compared to the molecular weight of native CAIX is equal to 427.5 Da (corresponds to MW (AV19-37)−MW (acetic acid)=486.52−60.052=426.5).

Mass spectrometry experiments were performed with an electrospray ionization time-of-flight mass spectrometer (Q-TOF) to show the covalent binding of compounds with the CA isozymes. The covalent binding of AV19-37 with eleven catalytically active CA isozymes was confirmed through MS experiments, except for CAIII isozyme, which did not show a covalent modification in the presence of ligand. Representative mass spectrometry data are shown in FIG. 3. Compound AV19-37 incubated with CAIX isozyme showed a major peak relating to protein-compound adduct with the mass shift equal to compound molecular mass without acetic acid (ΔMW=427.5, respectively) and minor set of peaks relating to two or three bind inhibitor molecules to the CAIX.

TABLE 1
The apparent dissociation constants $K_{d\_app}$ (nM) for compound interaction with human recombinant CA isozymes as determined by FTSA at 37° C. and pH 7.0.
| | | $K_{d\_app}$, nM | | | | |
|---|---|---|---|---|---|---|
| Cmpd | Structure | CAI | CAII | CAIII | CAIV | CAVA |
| AV21-03-2 | 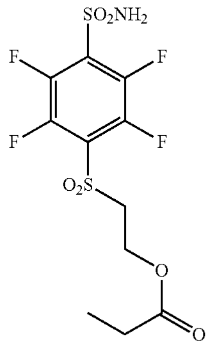 [SMILES: CCC(=O)OCCS(=O)(=O)c1c(F)c(F)c(S(N)(=O)=O)c(F)c1F] | 0.0025 | 0.067 | 40000 | 2.0 | 2.5 |
| AV22-162 | 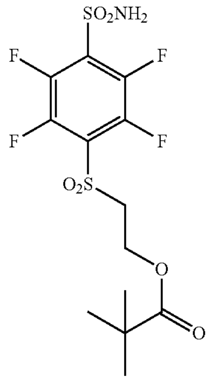 [SMILES: CC(C)(C)C(=O)OCCS(=O)(=O)c1c(F)c(F)c(S(N)(=O)=O)c(F)c1F] | 0.0084 | 0.35 | 15000 | 64 | nd |
| AV21-25 | 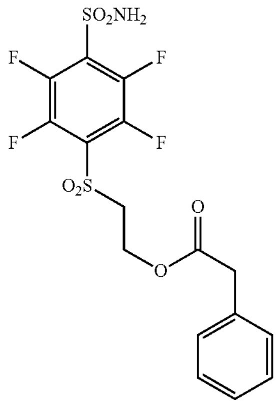 [SMILES: NS(=O)(=O)c1c(F)c(F)c(S(=O)(=O)CCOC(=O)Cc2ccccc2)c(F)c1F] | 0.0024 | 0.14 | 18000 | 45 | 2.5 |
| AV22-138-1 | 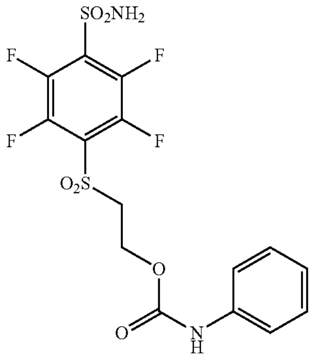 [SMILES: NS(=O)(=O)c1c(F)c(F)c(S(=O)(=O)CCOC(=O)Nc2ccccc2)c(F)c1F] | 0.0077 | 0.35 | 4200 | 16 | 1.3 |

TABLE 1-continued
The apparent dissociation constants $K_{d\_app}$ (nM) for compound interaction with human recombinant CA isozymes as determined by FTSA at 37° C. and pH 7.0.
| | | | | | | |
|---|---|---|---|---|---|---|
| AV23-04 | 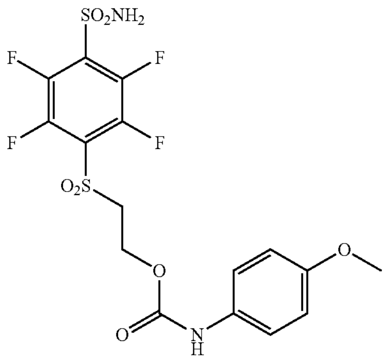 [SMILES: COc1ccc(NC(=O)OCCS(=O)(=O)c2c(F)c(F)c(S(N)(=O)=O)c(F)c2F)cc1] | 0.0031 | 0.3 | nd | 20 | nd |
| AV22-48 | 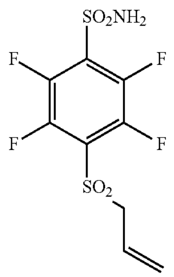 | 0.0067 | 0.29 | 29000 | 13 | 1.0 |
| AV19-37 | 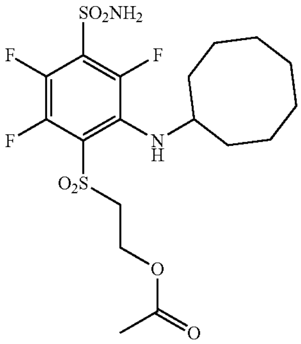 [SMILES: CC(=O)OCCS(=O)(=O)c1c(F)c(F)c(S(N)(=O)=O)c(F)c1NC1CCCCCCC1] | nd | 0.75 | ≥200000 | 1.1 | 540 |
| AV21-08 | 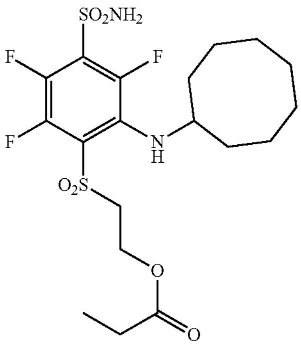 [SMILES: CCC(=O)OCCS(=O)(=O)c1c(F)c(F)c(S(N)(=O)=O)c(F)c1NC1CCCCCCC1] | nd | 0.75 | ≥200000 | 1.6 | 1000 |

TABLE 1-continued
The apparent dissociation constants $K_{d\_app}$ (nM) for compound interaction with human recombinant CA isozymes as determined by FTSA at 37° C. and pH 7.0.
| | | | | | | |
|---|---|---|---|---|---|---|
| AV21-47 | 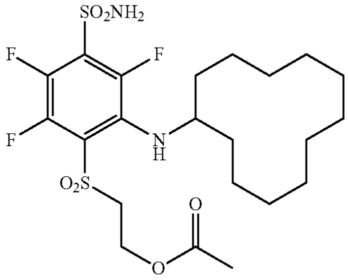 [SMILES: CC(=O)OCCS(=O)(=O)c1c(F)c(F)c(S(N)(=O)=O)c(F)c1NC1CCCCCCCCCCC1] | nd | 1.00 | ≥200000 | 0.20 | 5000 |
| AV22-132 | 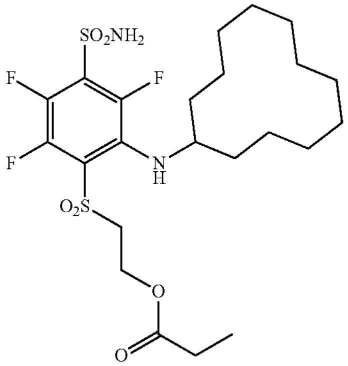 [SMILES: CCC(=O)OCCS(=O)(=O)c1c(F)c(F)c(S(N)(=O)=O)c(F)c1NC1CCCCCCCCCCC1] | 48 | 2.0 | ≥200000 | 4.0 | 3300 |
| AV22-149 | 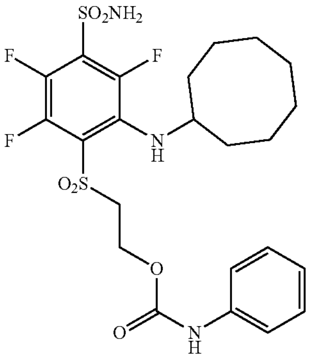 [SMILES: NS(=O)(=O)c1c(F)c(F)c(S(=O)(=O)CCOC(=O)Nc2ccccc2)c(NC2CCCCCCC2)c1F] | 22 | 1.2 | 120000 | 2.3 | nd |
| AV19-36 | 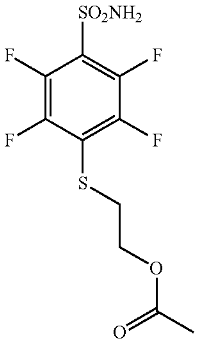 [SMILES: CC(=O)OCCSc1c(F)c(F)c(S(N)(=O)=O)c(F)c1F] | 0.20 | 11 | 50000 | 670 | 220 |
| | $K_{d\_app}$, nM | | | | | | |
|---|---|---|---|---|---|---|---|
| Cmpd | CAVB | CAVI | CAVII | CAIX | CAXII | CAXIII | CAXIV |
| AV21-03-2 | 0.012 | 0.050 | 0.0020 | 0.017 | 0.020 | 0.0033 | 0.10 |
| AV22-162 | nd | 0.29 | 0.78 | 0.089 | 0.34 | 0.053 | 1.1 |
| AV21-25 | 0.017 | 0.36 | 0.83 | 0.041 | 0.072 | 0.012 | 0.28 |
| AV22-138-1 | 0.0050 | 0.12 | 0.36 | 0.043 | 0.12 | 0.021 | 0.40 |
| AV23-04 | nd | 0.062 | 0.40 | 0.038 | 0.055 | 0.022 | 0.51 |
| AV22-48 | 0.010 | 0.29 | 0.0059 | 0.071 | 0.034 | 0.058 | 0.063 |

TABLE 1-continued

The apparent dissociation constants $K_{d\_app}$ (nM) for compound interaction with human recombinant CA isozymes as determined by FTSA at 37° C. and pH 7.0.

| | | | | | | | |
|---|---|---|---|---|---|---|---|
| AV19-37 | 3.5 | 10 | 0.041 | 0.0038 | 0.016 | 0.016 | 0.22 |
| AV21-08 | 0.020 | 2.5 | 0.050 | 0.0022 | 0.0071 | 0.011 | 0.32 |
| AV21-47 | 0.29 | 31 | nd | 0.0025 | 0.10 | 0.015 | 0.50 |
| AV22-132 | 0.20 | 1600 | nd | 0.0091 | 0.16 | 0.011 | 0.91 |
| AV22-149 | 0.11 | 40 | 77 | 0.0077 | 0.014 | 0.020 | 1.6 |
| AV19-36 | 18 | 670 | 5.0 | 20 | 220 | 3.6 | 3.6 |

The invention claimed is:

1. A composition comprising an effective amount of a fluorinated benzenesulfonamide compound that irreversibly binds to a carbonic anhydrase, wherein carbonic anhydrase is CAI, CAII, CAIV, CAVA, CAVB, CAVI, CAVII, CAIX, CAXII, CAXIII or CAXIV, wherein the fluorinated benzenesulfonamide compound is of structure I or a pharmaceutically acceptable salt thereof:

I

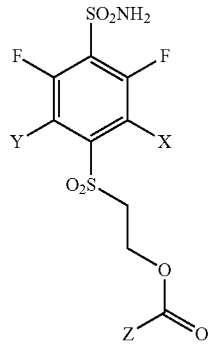

wherein X, Y are F or $NHR^1$, $NR^1R^2$ and Z is $R^3$ or $NHR^3$;

$R^1$ and $R^2$ are each independently selected from the group consisting of $R^4$, $R^5$, $R^6$, and $R^7$;

$R^4$ is cycloalkyl, cycloalkenyl, cycloalkynyl, heterocycloalkyl, heterocycloalkenyl or heterocycloalkynyl, each of which is unfused or fused with benzene, each of ring is unsubstituted or substituted on one or more carbon atoms with substituent independently chosen from $R^{12}$;

$R^5$ is alkyl, alkenyl or alkynyl each of which is unsubstituted or substituted on one or more carbon atoms with substituent independently chosen from $R^{12}$;

$R^6$ is phenyl, which is unfused or fused with benzene, heteroarene, cycloalkane or heterocycloalkane each of which is unsubstituted or substituted on one or more ring carbon atoms with substituent independently chosen from $R^{12}$;

$R^7$ is alkylphenyl, alkylheteroaryl each of which is unsubstituted or substituted on one or more carbon atoms with substituent independently chosen from $R^{12}$;

$R^3$ is selected from the group consisting of $R^8$, $R^9$, $R^{10}$, and $R^{11}$;

$R^8$ is cycloalkyl, cycloalkenyl, cycloalkynyl, heterocycloalkyl, heterocycloalkenyl or heterocycloalkynyl, each of which is unfused or fused with benzene, each of ring is unsubstituted or substituted on one or more carbon atoms with substituent independently chosen from $R^{12}$;

$R^9$ is alkyl, alkenyl or alkynyl each of which is unsubstituted or substituted on one or more carbon atoms with substituent independently chosen from $R^{12}$;

$R^{10}$ is phenyl, which is unfused or fused with benzene, cycloalkane or heterocycloalkane each of which is unsubstituted or substituted on one or more ring carbon atoms with substituent independently chosen from $R^{12}$;

$R^{11}$ is alkylphenyl, alkylheteroaryl each of which is unsubstituted or substituted on one or more carbon atoms with substituent independently chosen from $R^{12}$;

$R^{12}$ is F, Cl, Br, I, OH, $OR^{13}$, SH, $SR^{13}$, $S(O)R^{13}$, $SO_2R^{13}$, $C(O)R^{13}$, $C(O)OR^{13}$, $OC(O)R^{13}$, $C(O)N(R^{13})_2$, $C(O)NHR^{13}$, $C(O)N(CH_3)R^{13}$, $NHC(O)R^{13}$, $NR^{13}C(O)R^{13}$, $NHC(O)OR^{13}$, $NR^{13}C(O)OR^{13}$, $OC(O)N(R^{13})_2$, $OC(O)NHR^{13}$, $OC(O)NH_2$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $SO_2NH_2$, $SO_2NHR^{13}$, $SO_2N(R^{13})_2$, $NR^{13}SO_2R^{13}$, $NHSO_2NHR^{13}$, $NHSO_2N(R^{13})_2$, $NR^{13}SO_2NHR^{13}$, $NR^{13}SO_2N(R^{13})_2$, C(O)NHNHOH, $C(O)NHNHOR^{13}$, $C(O)NHSO_2R^{13}$, $C(O)NR^{13}SO_2R^{13}$, $C(NH)NH_2$, $C(NH)NHR^{13}$, $C(NH)N(R^{13})_2$, $N(CH_3)SO_2NHR^{13}$, $NHSO_2N(CH_3)R^{13}$, $N(CH_3)SO_2N(CH_3)R^{13}$, $NH_2$, $NHR^{13}$, $N(R^{13})_2$, $N(CH_3)C(O)N(R^{13})_2$, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$;

$R^{13}$ is alkyl, alkenyl or alkynyl, cycloalkyl, cycloalkenyl, cycloalkynyl, heterocycloalkyl, heterocycloalkenyl or heterocycloalkynyl, phenyl, which is unfused or fused with benzene, heteroarene, cycloalkane or heterocycloalkane; and wherein the fluorinated benzenesulfonamide compound does not comprise compound 2-{[4-aminosulfonyl)-2,3,5,6-tetrafluorophenyl]sulfonyl}ethyl acetate.

2. The composition according to claim 1, wherein the fluorinated benzenesulfonamide compound is selected from the group consisting of:

2-((2,3,5,6-tetrafluoro-4-sulfamoylphenyl)sulfonyl)ethyl propionate, 2-((2,3,5,6-tetrafluoro-4-sulfamoylphenyl)sulfonyl)ethyl 2-phenylacetate, 2-((2,3,5,6-tetrafluoro-4-sulfamoylphenyl)sulfonyl)ethyl pivalate, 2-((2-(cyclooctylamino)-3,5,6-trifluoro-4-sulfamoylphenyl)sulfonyl)ethyl acetate, 2-((2-(cyclooctylamino)-3,5,6-trifluoro-4-sulfamoylphenyl)sulfonyl)ethyl propionate, 2-((2-(cyclododecylamino)-3,5,6-trifluoro-4-sulfamoylphenyl)sulfonyl)ethyl acetate, 2-((2-(cyclododecylamino)-3,5,6-trifluoro-4-sulfamoylphenyl)sulfonyl)ethyl propionate, 2,3,5,6-tetrafluoro-4-(vinylsulfonyl)benzenesulfonamide, 2-((2,3,5,6-tetrafluoro-4-sulfamoylphenyl)sulfonyl)ethyl phenylcarbamate, 2-((2,3,5,6-tetrafluoro-4-sulfamoylphenyl)sulfonyl)ethyl (4-methoxyphenyl)carbamate, and 2-((2-(cyclooctylamino)-3,5,6-trifluoro-4-sulfamoylphenyl)sulfonyl)ethyl phenylcarbamate.

3. The composition of claim 1, wherein the fluorinated benzenesulfonamide compound forms a vinylsulfone group in the presence of a nucleophilic amino acid of the carbonic anhydrase and wherein the vinylsulfone group covalently binds to the nucleophilic amino acid of the carbonic anhydrase.

4. The pharmaceutical composition of claim 1, comprising pharmaceutically acceptable diluents, excipient, or carrier.

5. The pharmaceutical composition of claim 1 as part of a pharmaceutical formulation for use in treatment of conditions where irreversible inhibition of carbonic anhydrases is necessary and characterized in that the conditions are selected from eye disorders, including glaucoma, macular edema, diabetic macular edema, retinitis pigmentosa, hereditary retinoschisis, cataract, retinopathy, including chronic central serous chorioretinopathy, diabetic retinopathy, hypertensive retinopathy, and other disorders, including infantile nystagmus syndrome (INS), cerebral edema, edema, acute mountain sickness, bipolar disorder, chronic obstructive pulmonary disease (COPD), gastric ulcer, obesity, epilepsy, sleep apnea, migraine, diabetic injury, congestive heart failure, pulmonary hypertension, cariogenesis, cerebral ischemia, diabetic brain injury, angina, myocardial infarction, idiopathic intracranial hypertension, hydrocephalus, a range of cerebral pathologies, including traumatic brain injury and ischemic and hemorrhagic stroke, osteoporosis, pseudotumor cerebri, cancers, including renal cancer, pancreatic cancer, esophagus cancer, head and neck cancer, thyroid cancer, papillary/follicular carcinomas, nasopharyngeal cancer, breast cancer, ovarian cancer, vulva cancer, uterine cervix cancer, bladder cancer, skin cancer, squamous/basal cell carcinomas, liver cancer, lung cancer, brain cancers, and mesothelioma.

* * * * *